US009249470B2

(12) United States Patent
Hill et al.

(10) Patent No.: US 9,249,470 B2
(45) Date of Patent: Feb. 2, 2016

(54) METHOD FOR PREDICTING THE ATHLETIC PERFORMANCE POTENTIAL OF A SUBJECT

(71) Applicant: University College Dublin-National University of Ireland, Dublin, Dublin (IE)

(72) Inventors: Emmeline Hill, Dublin (IE); David MacHugh, Dublin (IE); JingJing Gu, Dublin (IE); Beatrice McGivney, County Roscommon (IE)

(73) Assignee: University College Dublin-National University of Ireland, Dublin (IE)

( * ) Notice: Subject to any disclaimer, the term of this patent is extended or adjusted under 35 U.S.C. 154(b) by 61 days.

(21) Appl. No.: 14/175,696

(22) Filed: Feb. 7, 2014

(65) Prior Publication Data
US 2014/0189894 A1  Jul. 3, 2014

Related U.S. Application Data

(60) Division of application No. 13/046,432, filed on Mar. 11, 2011, now abandoned, which is a continuation-in-part of application No. 13/063,715, filed as application No. PCT/IE2009/000062 on Sep. 11, 2009, now Pat. No. 8,771,943.

(60) Provisional application No. 61/136,533, filed on Sep. 11, 2008, provisional application No. 61/213,125, filed on May 8, 2009.

(30) Foreign Application Priority Data

Mar. 11, 2010 (IE) .................................... 2010/0151

(51) Int. Cl.
C12Q 1/68 (2006.01)
A01K 15/02 (2006.01)
A01K 67/02 (2006.01)

(52) U.S. Cl.
CPC .............. *C12Q 1/6888* (2013.01); *A01K 15/02* (2013.01); *A01K 67/02* (2013.01); *C12Q 2600/124* (2013.01); *C12Q 2600/156* (2013.01)

(58) Field of Classification Search
None
See application file for complete search history.

(56) References Cited

U.S. PATENT DOCUMENTS

2003/0092019 A1  5/2003  Meyer et al.
2008/0187928 A1  8/2008  Evans et al.
2011/0223600 A1  9/2011  Hill et al.

FOREIGN PATENT DOCUMENTS

WO  WO 2006/003436 A1  1/2006
WO  WO 2008/034177 A1  3/2008

OTHER PUBLICATIONS

Ballard et al., The Mitochondrial Genome: Mutation, Selection and Recombination, Current Opinion in Genetics & Development, vol. 11, pp. 667-672, (2001).
Barrett et al., Haploview: Analysis and Visualization of LD and Haplotype Maps, Bioinformatics, vol. 21, Issue 2, pp. 263-265, (2005).
Barrett, Haploview: Visualization and Analysis of SNP Genotype Data, Cold Spring Harbor Protocols, pp. 1-3, (2009).
Barrey et al., Heritability of Percentage of Fast Myosin Heavy Chains in Skeletal Muscles and Relationship with Performance, Equine Veterinary Journal, Suppl. vol. 30, pp. 289-292, (1999).
Binns et al., Identification of the Myostatin Locus (MSTN) as Having a Major Effect on Optimum Racing Distance in the Thoroughbred Horse in the USA, 2010, Animal Genetics, 41 (Suppl. 2), 154-158.
Blier, Pierre U., Natural Selection and the Evolution of mtDNA-Encoded Peptides: Evidence for Intergenomic Co-Adaptation, Trends in Genetics vol. 17, No. 7, pp. 400-406, (2001).
Bray et al., The Human Gene Map for Performance and Health-Related Fitness Phenotypes: The 2006-2007 Update, Medicine & Science in Sports & Exercise, pp. 34-72 (2009).
Buitrago et al., The Transcriptional Repressor Nab1 is a Specific Regulator of Pathological Cardiac Hypertrophy, Nature Medicine, vol. 11, No. 8, pp. 837-844, (2005).
Cartharius et al., MatInspector and Beyond: Promoter Analysis Based on Transcription Factor Binding Sites, Bioinformatics, vol. 21, No. 13, pp. 2933-2942 (2005).
Clop et al., A Mutation Creating a Potential Illegitimate MicroRNA Target Site in the Myostatin Gene Affects Muscularity in Sheep, Nature Genetics, vol. 38, No. 7, pp. 813-818 (2006).
Cunningham et al., Microsatellite Diversity, Pedigree Relatedness and the Contributions of Founder Lineages to Thoroughbred Horses, Animal Genetics, 32, pp. 360-364, (2001).
Das, The Role of Mitochondrial Respiration in Physiological and Evolutionary Adaptation, BioEssays, vol. 28, pp. 890-901, (2006).
Dempsey et al., Exercise-induced Arterial Hypoxemia, J. Appl. Physiol., vol. 87: pp. 1997-2006, (1999).
Eivers et al., Alterations in Oxidative Gene Expression in Equine Skeletal Muscle Following Exercise and Training, Physiological Genomics, vol. 40, pp. 83-93, (2010).
Flück, Functional, Structural and Molecular Plasticity of Mammalian Skeletal Muscle in Response to Exercise Stimuli, The Journal of Experimental Biology, vol. 209, pp. 2239-2248, (2006).
Fukuda et al., HIF-1 Regulates Cytochrome Oxidase Subunits to Optimize Efficiency of Respiration in Hypoxic Cells, Cell, vol. 129, pp. 111-122, (2007).
Gordon et al., Consed: A Graphical Tool for Sequence Finishing, Genome Res., vol. 8, pp. 195-202, (1998).

(Continued)

*Primary Examiner* — Jeanine A Goldberg
(74) *Attorney, Agent, or Firm* — Finnegan, Henderson, Farabow, Garrett & Dunner, LLP

(57) ABSTRACT

A method for predicting the athletic performance potential of a subject comprising the step of assaying a biological sample from a subject for a genetic variant in linkage disequilibrium with MSTN-66493737 (T/C) SNP. The invention also provides an assay for determining the athletic performance potential of a subject.

18 Claims, 10 Drawing Sheets

(56) References Cited

OTHER PUBLICATIONS

Gramkow et al., Correlation of Race Earnings with Velocity at Maximal Heart Rate During a Field Exercise Test in Thoroughbred Racehorses, Equine vet. J.. Suppl. 36, pp. 118-122, (2006).

Grobet et al., A Deletion in the Bovine Myostatin Gene Causes the Double-Muscled Phenotype in Cattle, Nature Genetics, vol. 17, pp. 71-74 (1997).

Gu et al., A Genome Scan for Positive Selection in Thoroughbred Horses, PLoS ONE, vol. 4(6): e5767, pp. 1-17, (2009).

Gu et al., Association of Sequence Variants in CKM (Creatine Kinase, Muscle) and COX4l2 (Cytochrome C Oxidase, Subunit 4, Isoform 2) Genes with Racing Performance in Thoroughbred Horses, Equine vet. J. 42 (Suppl. 38) 569-575 (2010).

Gunn, Muscle, Bone and Fat Proportions and Muscle Distribution of Thoroughbreds and Other Horses, Equine exercise physiology 2. Davis, CA: ICEEP; pp. 253-264 (1987).

Hallstrom et al., Balancing the Decision of Cell Proliferation and Cell Fate, Cell Cycle, vol. 8(4), pp. 532-535, (2009).

Harkins et al., Effect of Furosemide on Physiologic Variables in Exercising Horses, Am J Vet Res, vol. 54, No. 12, (1993).

Hill et al., A Genome-Wide SNP-Association Study Confirms a Sequence Variant (g.66493737C>T) in the Equine Myostatin (MSTN) Gene as the Most Powerful Predictor of Optimum Racing Distance for Thoroughbred Racehorses, BMC Genomics 11:552 (2010).

Hill et al., A Sequence Polymorphism in MSTN Predicts Sprinting Ability and Racing Stamina in Thoroughbred Horses, PLoS One, vol. 5, Issue 1, e8645 (2010).

Hill et al., Moderate and High Intensity Sprint Exercise Induce Differential Responses in COX4l2 and PDK4 Gene Expression in Thoroughbred Horse Skeletal Muscle, Equine vet. J. 42 (Suppl. 38) 576-581 (2010).

Hill et al., Targets of Selection in the Thoroughbred Genome Contain Exercise-Relevant Gene SNPs Associated with Elite Racecourse Performance, Animal Genetics, 41 (Suppl. 2), 56-63 (2010).

Hoppeler et al., Muscle Tissue Adaptations to Hypoxia, The Journal of Experimental Biology, vol. 204, pp. 3133-3139 (2001).

Jorgensen et al., Hypothesis-Driven Candidate Gene Association Studies: Practical Design and Analytical Considerations, American Journal of Epidemiology, vol. 170, No. 8, pp. 986-993, (2009).

Joulia, Dominique, Mechanisms Involved in the Inhibition of Myoblast Proliferation and Differentiation by Myostatin, Experimental Cell Research, vol. 286, pp. 263-275, (2003).

Langley et al., Myostatin Inhibits Myoblast Differentiation by Down-Regulating MyoD Expression, J. Biol. Chem, vol. 277, No. 51, pp. 49831-49840, (2002).

Love et al., Prevalence, Heritability and Significance of Musculoskeletal Conformational Traits in Thoroughbred Yearlings, Equine Veterinary Journal, vol. 38 (7), pp. 597-603, (2006).

Matoba et al., p53 Regulates Mitochondrial Respiration, Science, vol. 312, pp. 1650-1653, (2006).

McGivney et al., Transcriptional Adaptations Following Exercise in Thoroughbred Horse Skeletal Muscle Highlights Molecular Mechanisms that Lead to Muscle Hypertrophy, BMC Genomics, vol. 9, Issue 10, pp. 1-18 (2009).

McGivney, Beatrice A., Characterization of the Equine Skeletal Muscle Transcriptome Identifies Novel Functional Responses to Exercise Training, BMC Genomics, vol. 11: 398, 1-17 (2010).

McPherron et al., Double Muscling in Cattle Due to Mutations in the Myostatin Gene, Proc. Natl. Acad. Sci. USA, vol. 94, pp. 12457-12461, (1997).

McPherron et al., Regulation of Skeletal Muscle Mass in Mice by a New TGF-? Superfamily Member, Nature, vol. 387, (1997).

Meiklejohn et al., Positive and Negative Selection on the Mitochondrial Genome, Trends in Genetics, vol. 23 No. 6, Apr. 2007.

Mosher et al., A Mutation in the Myostatin Gene Increases Muscle Mass and Enhances Racing Performance in Heterozygote Dogs, PLoS Genet, vol. 3, Issue 5: e79, pp. 0779-0786, (2007).

Polager et al., p53 and E2f: Partners in Life and Death, Nat Rev Cancer, vol. 9, pp. 738-748 (2009).

Purcell et al., PLINK: A Tool Set for Whole-Genome Association and Population-Based Linkage Analyses, Am. J. Hum, Genet, vol. 81, pp. 559-575 (2007).

Revington, Haematology of the Racing Thoroughbred in Australia 2: Haematological Values Compared to Performance, Equine vet. J. 15 (2), 145-148 (1983).

Rivero et al., Journal of Applied Physiology, vol. 102, pp. 1871-1882, (2007).

Rivero et al., Muscle Fiber Type Composition and Fiber Size in Successfully and Unsuccessfully Endurance-Raced Horses, The American Physiological Society, J Appl Physiol 75, 1758-66 (1993).

Rozen et al., Primer3 on the WWW for General Users and for Biologist Programmers, Methods in Molecular Biology, vol. 132, pp. 365-386 (2000).

Saleem et al., Role of p53 in Mitochondrial Biogenesis and Apoptosis in Skeletal Muscle, Physiological Genomics, vol. 37, pp. 58-66, (2009).

Sambrook and Russell, Molecular Cloning—A Laboratory Manual on the Web, Cold Spring Harbor Laboratory Press, Cold Spring Harbor Laboratory Press (2001).

Schuelke et al., Myostatin Mutation Associated with Gross Muscle Hypertrophy in a Child, N Engl. J. Med., vol. 350, pp. 2682-2688, (2004).

Seaman et al., Exercise Induced Ventilation/Perfusion Inequality in the Horse, Equine vet. J. 27 (2) 104-109, (1995).

Tabor et al., Candidate-Gene Approaches for Studying Complex Genetic Traits: Practical Considerations, Nature Reviews, Genetics, vol. 3, pp. 391-397 (May 2002).

Taylor et al., Therapeutic Targets for Hypoxia-Elicited Pathways, Pharmaceutical Research, vol. 16, No. 10, pp. 1498-1505 (1999).

Thiel et al., The Human Transcriptional Repressor Protein NAB1: Expression and Biological Activity, Biochimica et Biophysica Acta 1493, 289-301 (2000).

Thomas et al., Myostatin, a Negative Regulator of Muscle Growth, Functions by Inhibiting Myoblast Proliferation, The Journal of Biological Chemistry, vol. 275, No. 51, pp. 40235-40243 (Dec. 22, 2000).

Tozaki et al., A Genome-Wide Association Study for Racing Performances in Thoroughbreds Clarifies a Candidate Region Near the MSTN Gene, 2010, Animal Genetics, 41 (Suppl. 2), 28-35.

van Baren et al., The PCR Suite, Applications Note, vol. 20, No. 4, pp. 591-593, (2004).

Van Deursen et al., Skeletal Muscles of Mice Deficient in Muscle Creatine Kinase Lack Burst Activity, Cell, vol. 74, 621-631 (Aug. 27, 1993).

Wade et al., Genome Sequence, Comparative Analysis, and Population Genetics of the Domestic Horse, Science 326, pp. 865-867 (2009).

Weber et al., Glucocorticoid Hormone Stimulates Mitochondrial Biogenesis Specifically in Skeletal Muscle, Endocrinology 143: 177-184 (2002).

Williamson et al., The Inheritance of Speed, Stamina and Other Racing Performance Characters in the Australian Thoroughbred, J. Anim. Breed. Genet. 115, 1-16 (1998).

Yang et al., Improving the Prediction of Complex Diseases by Testing for Multiple Disease-Susceptibility Genes, Am. J. Hum. Genet. 72:636-649, 2003.

Young et al., Left Ventricular Size and Systolic Function in Thoroughbred Racehorses and their Relationships to Race Performance, Journal of Applied Physiology, vol. 99, pp. 1278-1285, (2005).

Zhou et al., In Silico Detection and Characteristics of Novel microRNA Genes in the Equus Caballus Genome Using an Integrated Ab Initio and Comparative Genomic Approach, Genomics 94 125-131 (2009).

International Preliminary Examination Report mailed Mar. 24, 2011 in PCT/IE2009/000062.

XP-002558304, (2 pages).
XP-002558305, (2 pages).
XP-002558306, (2 pages).
XP-002558307, (2 pages).
XP-002558308, (3 pages).

(56) References Cited

OTHER PUBLICATIONS

Mosher et al., A Mutation in the Myostatin Gene Increases Muscle Mass and Enhances Racing Performance in Heterozygote Dogs, (2007), PLoS Genet 3(5): e79, pp. 0779-0786.
Burgomaster et al., Divergent Response of Metabolite Transport Proteins in Human Skeletal Muscle After Sprint Interval Training and Detraining, Am J. Physiol Regul Integr Comp Physiol 292: pp. R1970-R1976, (2007).
MacArthur et al., Genes and Human Elite Athletic Performance, Hum Genet (2005) 116: pp. 331-339.
Lucentini (The Scientist; 2004, vol. 24, p. 20).
Hirschhorn et al. (Genetics in Medicine. vol. 4, No. 2, pp. 45-61, Mar. 2002).
Ioannidis (Nature Genetics, vol. 29, pp. 306-309, Nov. 2001).
Zill et al. (Molecular Psychiatry, vol. 9, pp. 1030-1036, 2004).
Wall et al. (Nature Reviews Genetics, vol. 4, pp. 587-597, Aug. 2003).
Sargoizaei et al. (J. Dairy Sci., vol. 91, pp. 2106-2117, 2007).
Tang (GenBank Accession No. AY840554, Mar. 31, 2005).
Hill et al. (PLos One, vol. 5, No. 1, e8645, Jan. 2010).
Hill et al. (BMC Genomics, vol. 11, No. 552, Oct. 11, 2010).
Tozaki et al. (Animal Genetics, vol. 43, pp. 42-53, 2011).
EquCab2.0 (NCBI Assembly, The Genome Assembly Team, Oct. 29, 2007).
Equine SNP50 genotyping BeadChips (Oct. 2009).
Eaton et al., "Maximal accumulated oxygen deficit in thoroughbred horses" *J. Appl. Physiol*, 78(4):1564-1568 (1995).
Park et al., "Molecular characterization and mutational screening of the PRKAG3 gene in the horse" *Cytogenetic and Genome Research*, 102(104):211-216 (2003).
International Search Report and Written Opinion issued by the European Patent Office for International Patent Application No. PCT/IE2009/000062, mailed Jan. 12, 2010.

SEQUENCE LISTING

<160> NUMBER OF SEQ ID NOS: 38

<210> SEQ ID NO 1
<211> LENGTH: 24
<212> TYPE: DNA
<213> ORGANISM: Equus caballus
<220> FEATURE:
<221> NAME/KEY: misc_feature
<223> OTHER INFORMATION: MSTN 3'UTR PCR Forward Primer

<400> SEQUENCE: 1
tactcccaca aagatgtctc caat                                         24

<210> SEQ ID NO 2

-continued

```
<211> LENGTH: 23
<212> TYPE: DNA
<213> ORGANISM: Equus caballus
<220> FEATURE:
<221> NAME/KEY: misc_feature
<223> OTHER INFORMATION: MSTN 3'UTR PCR Reverse Primer

<400> SEQUENCE: 2
tgaatcacct cctgcattag act                                              23

<210> SEQ ID NO 3
<211> LENGTH: 20
<212> TYPE: DNA
<213> ORGANISM: Equus caballus
<220> FEATURE:
<221> NAME/KEY: misc_feature
<223> OTHER INFORMATION: MSTN 3'UTR Sequencing Primer 1 (Forward)

<400> SEQUENCE: 3
gaatggctga tgtcatcagg                                                  20

<210> SEQ ID NO 4
<211> LENGTH: 20
<212> TYPE: DNA
<213> ORGANISM: Equus caballus
<220> FEATURE:
<221> NAME/KEY: misc_feature
<223> OTHER INFORMATION: MSTN 3'UTR Sequencing Primer 1 (Reverse)

<400> SEQUENCE: 4
cctgatgaca tcagccattc                                                  20

<210> SEQ ID NO 5
<211> LENGTH: 20
<212> TYPE: DNA
<213> ORGANISM: Equus caballus
<220> FEATURE:
<221> NAME/KEY: misc_feature
<223> OTHER INFORMATION: MSTN 3'UTR Sequencing Primer 2 (Forward)

<400> SEQUENCE: 5
caaatctcaa cgttccattg                                                  20

<210> SEQ ID NO 6
<211> LENGTH: 20
<212> TYPE: DNA
<213> ORGANISM: Equus caballus
<220> FEATURE:
<221> NAME/KEY: misc_feature
<223> OTHER INFORMATION: MSTN 3'UTR Sequencing Primer 2 (Reverse)

<400> SEQUENCE: 6
caatggaacg ttgagatttg                                                  20

<210> SEQ ID NO 7
<211> LENGTH: 20
<212> TYPE: DNA
<213> ORGANISM: Equus caballus
<220> FEATURE:
<221> NAME/KEY: misc_feature
<223> OTHER INFORMATION: MSTN 5'UTR PCR Forward Primer

<400> SEQUENCE: 7
ctggtttgtg tctggttttc                                                  20

<210> SEQ ID NO 8
<211> LENGTH: 22
```

-continued

```
<212> TYPE: DNA
<213> ORGANISM: Equus caballus
<220> FEATURE:
<221> NAME/KEY: misc_feature
<223> OTHER INFORMATION: MSTN 5'UTR PCR Reverse Primer

<400> SEQUENCE: 8
cttttccttc ctgcttacat ac                                              22

<210> SEQ ID NO 9
<211> LENGTH: 20
<212> TYPE: DNA
<213> ORGANISM: Equus caballus
<220> FEATURE:
<221> NAME/KEY: misc_feature
<223> OTHER INFORMATION: MSTN 5'UTR Sequencing Primer 1 (Forward)

<400> SEQUENCE: 9
aacaaaacaa acaggcaccc                                                 20

<210> SEQ ID NO 10
<211> LENGTH: 20
<212> TYPE: DNA
<213> ORGANISM: Equus caballus
<220> FEATURE:
<221> NAME/KEY: misc_feature
<223> OTHER INFORMATION: MSTN 5'UTR Sequencing Primer 1 (Reverse)

<400> SEQUENCE: 10
gggtgcctgt ttgttttgtt                                                 20

<210> SEQ ID NO 11
<211> LENGTH: 23
<212> TYPE: DNA
<213> ORGANISM: Equus caballus
<220> FEATURE:
<221> NAME/KEY: misc_feature
<223> OTHER INFORMATION: MSTN 5'UTR Sequencing Primer 2 (Forward)

<400> SEQUENCE: 11
gtcaggaaaa caagtttctc aaa                                             23

<210> SEQ ID NO 12
<211> LENGTH: 23
<212> TYPE: DNA
<213> ORGANISM: Equus caballus
<220> FEATURE:
<221> NAME/KEY: misc_feature
<223> OTHER INFORMATION: MSTN 5'UTR Sequencing Primer 2 (Reverse)

<400> SEQUENCE: 12
tttgagaaac ttgttttcct gac                                             23

<210> SEQ ID NO 13
<211> LENGTH: 20
<212> TYPE: DNA
<213> ORGANISM: Equus caballus
<220> FEATURE:
<221> NAME/KEY: misc_feature
<223> OTHER INFORMATION: MSTN 5'UTR Sequencing Primer 3 (Forward)

<400> SEQUENCE: 13
gacagcgaga ttcattgtgg                                                 20

<210> SEQ ID NO 14
<211> LENGTH: 20
<212> TYPE: DNA
```

```
<213> ORGANISM: Equus caballus
<220> FEATURE:
<221> NAME/KEY: misc_feature
<223> OTHER INFORMATION: MSTN 5'UTR Sequencing Primer 3 (Reverse)

<400> SEQUENCE: 14
ccacaatgaa tctcgctgtc                                              20

<210> SEQ ID NO 15
<211> LENGTH: 20
<212> TYPE: DNA
<213> ORGANISM: Equus caballus
<220> FEATURE:
<221> NAME/KEY: misc_feature
<223> OTHER INFORMATION: MSTN 5'UTR Sequencing Primer 4 (Forward)

<400> SEQUENCE: 15
cctgtttgtg ctgattcttg                                              20

<210> SEQ ID NO 16
<211> LENGTH: 20
<212> TYPE: DNA
<213> ORGANISM: Equus caballus
<220> FEATURE:
<221> NAME/KEY: misc_feature
<223> OTHER INFORMATION: MSTN 5'UTR Sequencing Primer 4 (Reverse)

<400> SEQUENCE: 16
caagaatcag cacaaacagg                                              20

<210> SEQ ID NO 17
<211> LENGTH: 23
<212> TYPE: DNA
<213> ORGANISM: Equus caballus
<220> FEATURE:
<221> NAME/KEY: misc_feature
<223> OTHER INFORMATION: Forward primer for genotyping the Ins227bp
      polymorphism

<400> SEQUENCE: 17
atcagctcac ccttgactgt aac                                          23

<210> SEQ ID NO 18
<211> LENGTH: 23
<212> TYPE: DNA
<213> ORGANISM: Equus caballus
<220> FEATURE:
<221> NAME/KEY: misc_feature
<223> OTHER INFORMATION: reverse primer for genotyping the Ins227bp
      polymorphism

<400> SEQUENCE: 18
tcatctctct ggacatcgta ctg                                          23

<210> SEQ ID NO 19
<211> LENGTH: 403
<212> TYPE: DNA
<213> ORGANISM: Equus caballus
<220> FEATURE:
<221> NAME/KEY: misc_feature
<223> OTHER INFORMATION: MSTN EquCab2.0 66493737_T/C SNP
<220> FEATURE:
<221> NAME/KEY: variation
<222> LOCATION: (202)..(202)
<223> OTHER INFORMATION: y is t or c

<400> SEQUENCE: 19
agctaagcaa gtaattagca caaaaatttg aatgttatat tcaggctatc tcaaaagtta   60
```

```
gaaaatactg tctttagagc caggctgtca ttgtgagcaa atcactagc aatttctttt      120 attttggttc cccaagattg tttataaata aggtaaatct actccaggac tatttgatag      180
cagagtcata aaggaaaatt ayttggtgca ttataacctg attacttaat aaggagaaca      240
atattttgaa actgttgtgt cctgttaaa gtagataaag cactgggtaa agcaggatcg      300
cagacacatg gcacagaatc ttccgtgtca tgccttctct gtgaaggtgt ctgtctccct      360
ttccttgagt gtagttatga actgactgca aaaagaatat atg                        403

<210> SEQ ID NO 20
<211> LENGTH: 403
<212> TYPE: DNA
<213> ORGANISM: Equus caballus
<220> FEATURE:
<221> NAME/KEY: misc_feature
<223> OTHER INFORMATION: MSTN EquCab2.0 66494218_A/C SNP
<220> FEATURE:
<221> NAME/KEY: variation
<222> LOCATION: (202)..(202)
<223> OTHER INFORMATION: m is a or c

<400> SEQUENCE: 20
aggagattat taagcaatgt gcctgcctgg aaatgtgcac cccgggtgct ctcaacaata       60
gtactatggt caaggtgtaa gcaggactct gagctataac ctctttgatt aaaatgttta      120
tttattaggc attttatgat aattagctca tgattatcat tatgctatgt ttacttcatc      180 attttctta ctaatacatt amatttaaa aaatattttt cctaatctcc aggggaataa       240
ctttcaaaat ctaatatgtt aatttgtgaa gaacataaaa acactatgag aaatagttt      300 gagtaacaga agtcattttg gtgttcagca aatgctcaaa tgacctaaac gtctacaaat      360
ttcttccttc tctattatta gtgaaaaaaa cttgttatta taa                        403

<210> SEQ ID NO 21
<211> LENGTH: 401
<212> TYPE: DNA
<213> ORGANISM: Equus caballus
<220> FEATURE:
<221> NAME/KEY: misc_feature
<223> OTHER INFORMATION: BIEC2-417495 C/T SNP
<220> FEATURE:
<221> NAME/KEY: variation
<222> LOCATION: (201)..(201)
<223> OTHER INFORMATION: y is t or c

<400> SEQUENCE: 21
cataaggtca aatattttc ccatttccct cttttattaa aataccacat ttatttggaa       60
aatcattact cagctctatt gcttactaat tattttaaga tagaaaaaat attttgtcgc      120
aaagaaagat ttcaagacat ctttatggct atataaatat ttatgcatct ttttaaatac      180
cttgattgat tggttttaga ytgtctcaga ttccatctga tttctctgcc tccctgataa      240
accttcttca atctctgttc cctggcctat gaaggtcacc ttcaaaatat tatcacctt      300 atgtaatgat cagacacaaa gtctaaccat catctaaatt atttcaatat gaagcatgac      360 taataaaacca gtatgagtag ttttcaaagt gaacaggatt t                         401

<210> SEQ ID NO 22
<211> LENGTH: 401
<212> TYPE: DNA
<213> ORGANISM: Equus caballus
<220> FEATURE:
<221> NAME/KEY: misc_feature
<223> OTHER INFORMATION: BIEC2-417372 G/A SNP
```

```
<220> FEATURE:
<221> NAME/KEY: variation
<222> LOCATION: (201)..(201)
<223> OTHER INFORMATION: r is g or a

<400> SEQUENCE: 22
gcctggatat gaagcccata agaaatgtct ggcagtggtc tcttgagatc agaaagagaa    60
tgggagatta ggaagttaga ataggaagca agtgaggcag caggtagygg aggctaggtg   120
gcccatctgt gagttttttc cttctgaact ccttacaatt ctttataaaa ttccatgaag   180
gcctcatttc aagataaagg rgaagaaaat attttctcct aaaaaagctt aaacttaata   240
ttctacttct caaaaaaaat tcaaagaggc ctaatagatt gactgaaact ctaactgaaa   300
tttgcctcgc tttcccaaat tcttactgga gagggcaag gcctcgcccc tctcagaact   360
cttacatgag attgctgctt tccttagttt ctgatcactg t                       401

<210> SEQ ID NO 23
<211> LENGTH: 227
<212> TYPE: DNA
<213> ORGANISM: Equus caballus
<220> FEATURE:
<221> NAME/KEY: misc_feature
<223> OTHER INFORMATION: MSTN Ins227bp

<400> SEQUENCE: 23
ggggctggcc ccgtggccga gtggttaagt tcgtgcgctc cgctgcaggc ggcccagtgt    60
ttcgtcggtt cgagtcctgg gcgcggacat ggcactgctc gtcggaccac gctgaggcag   120
cgtcccacat gccacaacta gaggaaccca caacgaagaa tacacaacta tgtaccgggg   180
ggctttgggg agaaaagga aataaaatc tttaaaaagc cacttgg                   227

<210> SEQ ID NO 24
<211> LENGTH: 422
<212> TYPE: DNA
<213> ORGANISM: Equus caballus
<220> FEATURE:
<221> NAME/KEY: misc_feature
<223> OTHER INFORMATION: MSTN 3'UTR SNP 1
<220> FEATURE:
<221> NAME/KEY: variation
<222> LOCATION: (203)..(203)
<223> OTHER INFORMATION: m is a or c

<400> SEQUENCE: 24
tatataccat cattttgatt atccttatac acttgaattt atattgtata atagcatact    60
tggtaagatg aaattccaca aaaataggaa tggtacacca tatgcaagtt tccattccta   120
ttgtgattga tacagtacat taacaatcca caccaatggt gctaatacaa ataggctgaa   180
tggctgatgt catcaggttt atmaaataaa aacatccaat aaaataatgt ttctcctttc   240
ttcaggtgca ttttccaaat ggggaatgga ttttctttaa tgaaagaaga atcattttc   300 tagaggtcag gatttaattc tgtagcatac ttggagaaac tgcattacct taaaaggcag   360
ccaaaaagta ttcattttta tcaaaatttc aaaattgcag cctgcttttg caacattgca   420
gt                                                                  422

<210> SEQ ID NO 25
<211> LENGTH: 484
<212> TYPE: DNA
<213> ORGANISM: Equus caballus
<220> FEATURE:
<221> NAME/KEY: misc_feature
<223> OTHER INFORMATION: MSTN 3'UTR SNP 2
```

```
<220> FEATURE:
<221> NAME/KEY: variation
<222> LOCATION: (232)..(232)
<223> OTHER INFORMATION: y is c or t

<400> SEQUENCE: 25
atccaataaa ataatgtttc tcctttcttc aggtgcattt tccaaatggg gaatggattt    60
tctttaatga aagaagaatc attttttctag aggtcaggat ttaattctgt agcatacttg   120
gagaaactgc attaccttaa aaggcagcca aaaagtattc attttttatca aaatttcaaa  180 attgcagcct gcttttgcaa cattgcagtt tttatgataa aataatggaa aygactgatt   240
ctgtcaatat tgtataaaaa gactttgaga caattgcatt tatataatat gtatacaata  300 ttgttttttgt aaataagcgt ctccttttttt atttactttg gtatattttt acagtcagaa 360
catttcaaat taagtattaa ggcacaaaga catgtcatgt atgacagaaa agcaactgct   420
tatatttcgg ggcaaattag cagattaaat agtggtctta aaactccata tgctaatggt  480
taga                                                                484

<210> SEQ ID NO 26
<211> LENGTH: 542
<212> TYPE: DNA
<213> ORGANISM: Equus caballus
<220> FEATURE:
<221> NAME/KEY: misc_feature
<223> OTHER INFORMATION: MSTN 3'UTR SNP 3
<220> FEATURE:
<221> NAME/KEY: variation
<222> LOCATION: (243)..(243)
<223> OTHER INFORMATION: r is g or a

<400> SEQUENCE: 26
atccaataaa ataatgtttc tcctttcttc aggtgcattt tccaaatggg gaatggattt    60
tctttaatga aagaagaatc attttttctag aggtcaggat ttaattctgt agcatacttg   120
gagaaactgc attaccttaa aaggcagcca aaaagtattc attttttatca aaatttcaaa  180 attgcagcct gcttttgcaa cattgcagtt tttatgataa aataatggaa atgactgatt   240
ctrtcaatat tgtataaaaa gactttgaga caattgcatt tatataatat gtatacaata  300 ttgttttttgt aaataagcgt ctccttttttt atttactttg gtatattttt acagtcagaa 360
catttcaaat taagtattaa ggcacaaaga catgtcatgt atgacagaaa agcaactgct   420
tatatttcgg ggcaaattag cagattaaat agtggtctta aaactccata tgctaatggt  480
tagatggtta tattcaatc attttatatt ttttacatt attaacattc acttatagat      540
tc                                                                  542

<210> SEQ ID NO 27
<211> LENGTH: 293
<212> TYPE: DNA
<213> ORGANISM: Equus caballus
<220> FEATURE:
<221> NAME/KEY: misc_feature
<223> OTHER INFORMATION: MSTN 3'UTR SNP 4
<220> FEATURE:
<221> NAME/KEY: variation
<222> LOCATION: (154)..(154)
<223> OTHER INFORMATION: w is a or t

<400> SEQUENCE: 27
tcaatttcca aatgcattgc agttggcaag ggtatatggt cctagagtta caagttctac    60
tgaagccaca ggaacacagg gaagctgcat cttttttttct agcacttaat gataccagca  120
```

```
catttatctg agctttgggg gtaccaattt tcawattgaa ttgaaaaata atcataaagt    180
gcctagaaat tcttaagtgc aacactgtac ataaatgttt ttgaagtgaa ctctcttctc    240
tactgcttat cagtttagta agttagctat aaagcagtga ctaagtctat gag           293

<210> SEQ ID NO 28
<211> LENGTH: 25
<212> TYPE: DNA
<213> ORGANISM: Equus caballus
<220> FEATURE:
<221> NAME/KEY: misc_feature
<223> OTHER INFORMATION: MSTN polymorphism genotyping forward primer

<400> SEQUENCE: 28
ccaggactat ttgatagcag agtca                                           25

<210> SEQ ID NO 29
<211> LENGTH: 31
<212> TYPE: DNA
<213> ORGANISM: Equus caballus
<220> FEATURE:
<221> NAME/KEY: misc_feature
<223> OTHER INFORMATION: MSTN polymorphism genotyping reverse primer

<400> SEQUENCE: 29
gacacaacag tttcaaaata ttgttctcct t                                    31

<210> SEQ ID NO 30
<211> LENGTH: 17
<212> TYPE: DNA
<213> ORGANISM: Equus caballus
<220> FEATURE:
<221> NAME/KEY: misc_feature
<223> OTHER INFORMATION: MSTN polymorphism genotyping probe

<400> SEQUENCE: 30
aatgcaccaa gtaattt                                                    17

<210> SEQ ID NO 31
<211> LENGTH: 16
<212> TYPE: DNA
<213> ORGANISM: Equus caballus
<220> FEATURE:
<221> NAME/KEY: misc_feature
<223> OTHER INFORMATION: MSTN polymorphism genotyping probe

<400> SEQUENCE: 31
atgcaccaaa taattt                                                     16

<210> SEQ ID NO 32
<211> LENGTH: 20
<212> TYPE: DNA
<213> ORGANISM: Equus caballus
<220> FEATURE:
<221> NAME/KEY: misc_feature
<223> OTHER INFORMATION: TTN forward primer

<400> SEQUENCE: 32
gcatgacaca actggaaagc                                                 20

<210> SEQ ID NO 33
<211> LENGTH: 20
<212> TYPE: DNA
<213> ORGANISM: Equus caballus
<220> FEATURE:
<221> NAME/KEY: misc_feature
<223> OTHER INFORMATION: TTN reverse primer
```

<400> SEQUENCE: 33
aactttgccc tcatcaatgc                                            20

<210> SEQ ID NO 34
<211> LENGTH: 20
<212> TYPE: DNA
<213> ORGANISM: Equus caballus
<220> FEATURE:
<221> NAME/KEY: misc_feature
<223> OTHER INFORMATION: MSTN1-2 forward primer

<400> SEQUENCE: 34
tgacagcagt gatggctctt                                            20

<210> SEQ ID NO 35
<211> LENGTH: 20
<212> TYPE: DNA
<213> ORGANISM: Equus caballus
<220> FEATURE:
<221> NAME/KEY: misc_feature
<223> OTHER INFORMATION: MSTN1-2 reverse primer

<400> SEQUENCE: 35
ttgggttttc cttccacttg                                            20

<210> SEQ ID NO 36
<211> LENGTH: 20
<212> TYPE: DNA
<213> ORGANISM: Equus caballus
<220> FEATURE:
<221> NAME/KEY: misc_feature
<223> OTHER INFORMATION: MSTN2-3 forward primer

<400> SEQUENCE: 36
ttcccaagac caggagaaga                                            20

<210> SEQ ID NO 37
<211> LENGTH: 20
<212> TYPE: DNA
<213> ORGANISM: Equus caballus
<220> FEATURE:
<221> NAME/KEY: misc_feature
<223> OTHER INFORMATION: MSTN2-3 reverse primer

<400> SEQUENCE: 37
cagcatcgag attctgtgga                                            20

<210> SEQ ID NO 38
<211> LENGTH: 467
<212> TYPE: DNA
<213> ORGANISM: Equus caballus
<220> FEATURE:
<221> NAME/KEY: misc_feature
<223> OTHER INFORMATION: MSTN Ins227bp and flanking sequences
<220> FEATURE:
<221> NAME/KEY: misc_feature
<222> LOCATION: (115)..(341)
<223> OTHER INFORMATION: MSTN Ins227bp

<400> SEQUENCE: 38
ttgtgacaga cagggtttta acctctgaca gcgagattca ttgtggagca ggagccaatc    60
atagatcctg acgacacttg tctcatcaaa gttggaatat aaaaagccac ttgggggct    120 ggccccgtgg ccgagtggtt aagttcgtgc gctccgctgc aggcggccca gtgtttcgtc    180
ggttcgagtc ctgggcgcgg acatggcact gctcgtcgga ccacgctgag gcagcgtccc    240

```
acatgccaca actagaggaa cccacaacga agaatacaca actatgtacc gggggctttt    300
ggggagaaaa aggaaaataa aatctttaaa aagccacttg gaatacagta taaaagattc    360
actggtgtgg caagttgtct ctcagactgt acaggcatta aaattttgct tggcattgct    420
caaaagcaaa agaaaagtaa aaggaagaaa taagagcaag gaaaaag                  467
```

METHOD FOR PREDICTING THE ATHLETIC PERFORMANCE POTENTIAL OF A SUBJECT

PRIOR APPLICATION

This is a Continuation of application Ser. No. 13/046,432, filed Mar. 11, 2011, which is a Continuation in Part of Ser. No. 13/063,715, filed May 27, 2011, which is a National Stage Entry of PCT/IE2009/000062, filed Sep. 11, 2009, which claims the benefit of U.S. Provisional Application No. 61/213,125, filed May 8, 2009 and U.S. Provisional Application No. 61/136,533, filed Sep. 11, 2008, all of which are incorporated herein by reference.

The invention relates to a method for predicting the athletic performance potential of a subject.

INTRODUCTION

Myostatin gene (MSTN) variants have previously been shown to contribute to muscle hypertrophy in a range of mammalian species (Grobet et al. 1997; McPherron et al. 1997; McPherron & Lee 1997; Schuelke et al. 2004; Mosher et al. 2007). In particular, whippet racing dogs that are heterozygote for a MSTN polymorphism have significantly greater racing ability than both homozygote wild-type dogs and homozygotes for the mutation that have an increased musculature that is detrimental to performance (Mosher et al. 2007). Horses, in particular Thoroughbreds, have a very high muscle mass to body weight ratio (55%) compared to other mammalian species (30-40%) (Gunn 1987) and the Thoroughbred genome contains evidence for selection for muscle strength phenotypes (Gu et al. 2009).

The Thoroughbred horse industry is a multi-billion dollar international enterprise engaged in the breeding, training and racing of elite racehorses. A Thoroughbred is a registered racehorse that can trace its ancestry to one of three foundation stallions and the approximately 30 foundation mares entered in The General Studbook, 1791 (Weatherby and Sons 1791). During the 300-year development of the breed racehorses have been intensely selected for athletic phenotypes that enable superior racecourse performance in particular types of races. There are two types of Thoroughbred race: National Hunt races are run over hurdles or steeplechase fences over distances of up to 4.5 miles (7,200 m), while Flat races have no obstacles and are run over distances ranging from five furlongs (⅝ mile or 1,006 m) to 20 furlongs (4,024 m). The International Federation of Horseracing Authorities recognizes five race distance categories: Sprint (5-6.5 f, ≤1,300 m), Mile (6.51-9.49 f, 1,301-1,900 m), Intermediate (9.5-10.5 f, 1,901-2,112 m), Long (10.51-13.5 f, 2,114-2,716 m) and Extended (>13.51 f, >2,717 m) races (International Federation of Horseracing Authorities Classifications, www-.horseracingintfed.com) [Note: 1 furlong=⅛ mile=201.2 meters] and horses that compete in these races are generally termed 'sprinters' (<6 furlongs), 'middle distance' or 'milers' (7-8 f) or 'stayers' (>8 f). Similar to their human counterparts, sprint racing Thoroughbreds are generally more compact and muscular than horses suited to longer distance races.

A range of approaches has been taken to investigate measurable associations with athletic performance phenotypes in Thoroughbred racehorses including assessment of heart size (Young et al 2005), muscle fibre type (Rivero et al. 2007) musculoskeletal conformation (Love et al 2006), speed at maximum heart rate (Gramkow & Evans 2006), haematological (Revington 1983) and other physiological variables (Harkins et al 1993).

WO2006003436 describes the association between performance and gene variants encoded by the mitochondrial genome. However, mitochondrial DNA (mtDNA) haplotypes are inherited strictly from the maternal parent and therefore relate solely to female contributions to the phenotype. As there is a limited number of mtDNA haplotypes (n=17) in the Thoroughbred population and just 10 females contribute to 74% of present maternal lineages (Cunningham et al 2002) it is unlikely that these haplotype variants have a significant effect as the favourable haplotypes would become 'fixed' quickly in a population where there is targeted selection for performance; in addition, the effective population size (of mtDNA variants) is one third of nuclear-encoded variants (Ballard and Dean 2001, Blier et al 2001, Das 2006, Meiklejohn et al 2007). Also, mtDNA haplotypes can be directly inferred from pedigree information.

It is an object of the invention to provide a method for predicting the athletic performance potential of a subject.

STATEMENTS OF INVENTION

The invention provides a method for predicting the athletic performance potential of a subject comprising the step of:
  assaying a biological sample from a subject for a genetic variant in linkage disequilibrium with MSTN-66493737 (T/C) SNP.

The subject may be an equine. The genetic variant may be located in equine chromosome 18. The genetic variant may be located in the MSTN gene region. The genetic variant may be located in the MSTN gene flanking region. The genetic variant may be chosen from one or more of: BIEC2-417495 SNP, BIEC2-417372 SNP, MSTN Ins227 bp mutation, MSTN 3'UTR SNP1, MSTN 3'UTR SNP2, MSTN 3'UTR SNP3, or MSTN 3'UTR SNP4. The genetic variant may be BIEC2417495 SNP. The presence of a C allele may be indicative of elite athletic performance. The presence of a heterozygous CT genotype may be indicative of elite athletic performance. The presence of a homozygous CC genotype may be indicative of elite athletic performance.

The elite athletic performance may be elite sprinting performance.

The biological sample of the subject may be chosen from one or more of: blood, saliva, skeletal muscle, hair, semen, bone marrow, soft tissue, internal organ biopsy sample or skin.

The invention also provides an assay for determining the athletic performance potential of a subject comprising the steps of:
  obtaining a biological sample from the subject;
  extracting or releasing DNA from the biological sample; and
  identifying a genetic variant in linkage disequilibrium with MSTN-66493737 (T/C) SNP in the biological sample
  wherein the athletic performance potential of the subject is associated with the genetic variant and/or the MSTN-66493737 (T/C) SNP.

The DNA may be genomic DNA.
The assay may further comprise the step of:
  amplifying a target sequence in the extracted or released DNA
  prior to the step of identifying a genetic variant in linkage disequilibrium with MSTN-66493737 (T/C) SNP The subject may be an equine. The genetic variant may be located in equine chromosome 18. The genetic variant may be located in the MSTN gene region. The genetic variant may be located in the MSTN gene flanking region. The genetic variant may be chosen from one or more of: BIEC2-417495 SNP, BIEC2-417372 SNP, MSTN Ins227 bp mutation, MSTN 3'UTR SNP1, MSTN 3'UTR SNP2, MSTN 3'UTR SNP3, or MSTN 3'UTR SNP4.

The genetic variant may be BIEC2417495 SNP. The presence of a C allele may be indicative of elite athletic performance. The presence of a heterozygous CT genotype may be indicative of elite athletic performance. The presence of a homozygous CC genotype may be indicative of elite athletic performance.

The elite athletic performance may be elite sprinting performance.

The biological sample of the subject may be chosen from one or more of: blood, saliva, skeletal muscle, hair, semen, bone marrow, soft tissue, internal organ biopsy sample or skin.

The invention further provides a method for predicting the athletic performance potential of a subject comprising the step of:
  assaying a biological sample from a subject for the presence of (i) a MSTN-66493737 (T/C) SNP and (ii) a genetic variant in linkage disequilibrium with the MSTN-66493737 (T/C) SNP.

The subject may be an equine. The genetic variant may be located in equine chromosome 18. The genetic variant may be located in the MSTN gene region. The genetic variant may be located in the MSTN gene flanking region. The genetic variant may be chosen from one or more of: BIEC2-417495 SNP, BIEC2-417372 SNP, MSTN Ins227 bp mutation, MSTN 3'UTR SNP1, MSTN 3'UTR SNP2, MSTN 3'UTR SNP3, or MSTN 3'UTR SNP4.

The genetic variant may be BIEC2417495 SNP. The presence of a C allele in the BIEC2417495 SNP may be indicative of elite athletic performance. The presence of a heterozygous CT genotype in the BIEC2417495 SNP may be indicative of elite athletic performance. The presence of a homozygous CC genotype in the BIEC2417495 SNP may be indicative of elite athletic performance.

The presence of C allele in the MSTN-66493737 (T/C) SNP may be indicative of elite athletic performance. The presence of a heterozygous CT genotype in the MSTN-66493737 (T/C) SNP may be indicative of elite athletic performance. The presence of a homozygous CC genotype in the MSTN-66493737 (T/C) SNP may be indicative of elite athletic performance.

The elite athletic performance may be elite sprinting performance.

The biological sample of the subject may be chosen from one or more of: blood, saliva, skeletal muscle, hair, semen, bone marrow, soft tissue, internal organ biopsy sample or skin.

The invention also provides an assay for determining the athletic performance potential of a subject comprising the steps of:
  obtaining a biological sample from the subject;
  extracting or releasing DNA from the biological sample; and
  identifying (i) a MSTN-66493737 (T/C) SNP and (ii) a genetic variant in linkage disequilibrium with the MSTN-66493737 (T/C) SNP in the biological sample
  wherein the athletic performance potential of the subject is associated with the MSTN-66493737 (T/C) SNP and/or the genetic variant.

The DNA may be genomic DNA.

The assay may further comprise the step of:
  amplifying a target sequence in the extracted or released DNA
  prior to the step of identifying (i) a MSTN-66493737 (T/C) SNP and (ii) a genetic variant in linkage disequilibrium with the MSTN-66493737 (T/C) SNP in the biological sample.

The subject may be an equine. The genetic variant may be located in equine chromosome 18. The genetic variant may be located in the MSTN gene region. The genetic variant may be located in the MSTN gene flanking region. The genetic variant may be chosen from one or more of: BIEC2-417495 SNP, BIEC2-417372 SNP, MSTN Ins227 bp mutation, MSTN 3'UTR SNP1, MSTN 3'UTR SNP2, MSTN 3'UTR SNP3, or MSTN 3'UTR SNP4.

The genetic variant may be BIEC2417495 SNP. The presence of a C allele in the BIEC2417495 SNP may be indicative of elite athletic performance. The presence of a heterozygous CT genotype in the BIEC2417495 SNP may be indicative of elite athletic performance. The presence of a homozygous CC genotype in the BIEC2417495 SNP may be indicative of elite athletic performance.

The presence of C allele in the MSTN-66493737 (T/C) SNP may be indicative of elite athletic performance. The presence of a heterozygous CT genotype in the MSTN-66493737 (T/C) SNP may be indicative of elite athletic performance. The presence of a homozygous CC genotype in the MSTN-66493737 (T/C) SNP may be indicative of elite athletic performance.

The elite athletic performance may be elite sprinting performance.

The biological sample of the subject may be chosen from one or more of: blood, saliva, skeletal muscle, hair, semen, bone marrow, soft tissue, internal organ biopsy sample or skin.

The invention further provides a method for predicting the athletic performance potential of a subject comprising the step of assaying a biological sample from a subject for the presence of a DNA polymorphism (SNP or insertion) in the MSTN gene and/or flanking sequences.

The DNA polymorphism may be an insertion polymorphism. The polymorphism may be Chr18g.66495327Ins227 bp66495326. The presence of a Ins227 bp allele may be indicative of elite athletic performance. The presence of a homozygous Ins227 bp/Ins227 bp genotype may be indicative of elite athletic performance. The elite athletic performance may be elite sprinting performance. The biological sample of the subject may be selected from the group comprising: blood, saliva, skeletal muscle, hair, semen, bone marrow, soft tissue, internal organ biopsy sample and skin.

The subject may be from a competitive racing species. The subject may be an equine. The subject may be chosen from one or more of a thoroughbred race horse, a standardbred trotter, a French trotter, a Quarter horse, or a competitive jumping horse.

The invention further provides an assay for determining the athletic performance potential of a subject comprising the steps of:
  obtaining a sample;
  extracting or releasing DNA from the sample; and
  identifying a polymorphism (SNP or insertion) in a target sequence from an MSTN gene associated with athletic performance in the extracted or released DNA
  wherein the athletic performance potential of a subject is associated with the polymorphism.

The polymorphism may be an insertion polymorphism. The polymorphism may be Chr18g.66495327Ins227 bp66495326. The presence of a Ins227 bp allele may be indicative of elite athletic performance. The presence of a homozygous Ins227 bp/Ins227 bp genotype may be indicative of elite athletic performance. The elite athletic performance may be elite sprinting performance The assay may comprise the step of:
amplifying a target sequence from a gene associated with athletic performance in the extracted or released DNA prior to the step of identifying a DNA polymorphism.

The DNA may be genomic DNA

The invention also provides an assay for use in determining the athletic performance potential of a subject comprising a detector for detecting the presence of a polymorphism (SNP or insertion) in the MSTN gene and/or flanking sequences.

The polymorphism may be an insertion polymorphism. The polymorphism may be Chr18g.66495327Ins227 bp66495326. The presence of a Ins227 bp allele may be indicative of elite athletic performance. The presence of a homozygous Ins227 bp/Ins227 bp genotype may be indicative of elite athletic performance. The elite athletic performance may be elite sprinting performance The invention further provides an assay for determining the athletic potential of a subject comprising the step of:
obtaining a sample;
extracting or releasing DNA from the sample; and
identifying the genotype of the Chr18g.66495327Ins227 bp66495326 polymorphism in the extracted or released DNA
wherein the presence of a Ins227 bp allele in the Chr18g.66495327Ins227 bp66495326 polymorphism is indicative of elite athletic performance.

The assay may comprise the step of:
amplifying a target sequence encoding the Chr18g.66495327Ins227 bp66495326 polymorphism in the extracted or released DNA
prior to the step of identifying the genotype of the Chr18g.66495327Ins227 bp66495326 polymorphism.

The presence of a homozygous Ins227 bp/Ins227 bp genotype may be indicative of elite athletic performance. The elite athletic performance may be elite sprinting performance.

The DNA may be genomic DNA.

The subject may be from a competitive racing species. The subject may be an equine. The subject may be chosen from one or more of a thoroughbred race horse, a standardbred trotter, a French trotter, a Quarter horse, or a competitive jumping horse.

The invention further provides a MSTN insertion mutation encoded by the DNA sequence of SEQ ID No. 23.

This invention provides DNA-based tests for detecting structural genetic variation in nuclear-encoded genes.

The methods and assays described herein are performed ex vivo and can be considered to be ex vivo or in vitro methods and assays.

Any suitable biological sample which contains genetic material for example, blood, saliva, hair, skin, bone marrow, soft tissue, internal organs, biopsy sample, semen, skeletal muscle tissue and the like, may be used as a biological sample for the methods described herein. Blood and hair samples are particularly suitable as a biological sample.

"Athletic performance" as used herein includes racing such as competitive racing and equestrian sports such as racing, showjumping, trotting, eventing, dressage, endurance events, riding, hunting and the like. The equestrian sports may be competitive sports. Of particular importance is sprint racing performance.

Competitive racing species include equines (horses), camels, dogs, elephants, hares, kangaroos, ostriches, pigeons, Homo sapiens and birds of prey such as hawks or falcons. The competitive racing species may be a competition horse such as a Thoroughbred race horse, Standardbred Trotter, French Trotter, Quarter Horse or a competitive jumping horse.

By "primer" we mean a nucleic acid sequence containing between about 15 to about 40 for example between about 18 to about contiguous nucleotides from a nucleic acid sequence of interest. The primer may be a forward (5' or 3') or reverse (3' to 5') primer or a primer designed on a complementary nucleic acid sequence to the sequence of interest. In the present invention, the sequence of interest is the genomic sequence of a gene associated with athletic performance, for example myostatin. In one embodiment, the primer may comprise between about 15 to about 40 nucleotides. By "complementary sequence" we mean a sequence that binds to the sequence of interest using conventional Watson-Crick base pairing i.e. adenine binds to thymine and cytosine binds to guanine.

In our PCT/IE2009/000062, the entire contents of which is incorporated herein by reference, we describe the association between athletic performance and single nucleotide polymorphisms for example a single polymorphism (g.66493737C>T) in the myostatin gene. Novel sequence variants were identified by re-sequencing the equine MSTN gene in 24 unrelated Thoroughbred horses using 13 overlapping primer pairs spanning all three exons and 288 bp of the 5' upstream region. Although no exonic sequence variants were detected, six SNPs were detected in intron 1 of MSTN [nt 66492979-66494807]. There was a highly significant ($P=3.70\times10^{-5}$) association with g.66493737C>T and elite short distance ($\leq 8$ f) racing performance and this association became marginally stronger ($P=1.88\times10^{-5}$) when the short distance cohort was further subdivided into animals (n=43) that had won their best race over distances$\leq 7$ f. The C allele was twice as frequent in the short distance ($\leq 7$ f) than in the long distance (>8 f) cohort (0.72 and 0.36 respectively) corresponding to an odds ratio of 4.54 (95% C.I. 2.23-9.23). The most parsimonious model was the genotypic model ($P=1.18\times10^{-6}$) indicating that genotypes are predictive of optimum racing distance. Considering best race distance (BRD) as a quantitative trait, we analyzed the data for the elite cohort using the distance (furlongs) of the highest grade or most valuable Group race won as the phenotype (n=79). BRD was highly significantly associated ($P=4.85\times10^{-8}$) with the g.66493737C>T SNP. This result was independently validated ($P=1.91\times10^{-6}$) in a re-sampled group of unrelated elite (Group and Listed race winners) Thoroughbreds (n=62) and in a cohort of 37 elite racehorses (P=0.0047) produced by the same trainer. For each genotype we determined the mean BRD in the original sample: C/C mean=6.2±0.8 f; C/T mean=9.1±2.4 f; and T/T mean=10.5±2.7 f.

The invention provides structural DNA polymorphisms (including insertion polymorphisms and single nucleotide polymorphisms) that are associated with elite athletic performance. The invention provides a method of predicting the athletic performance of a subject comprising the step of assaying a biological sample from the subject for the presence of a structural DNA polymorphism (SNP or insertion) in MSTN wherein the polymorphism has a significant association with athletic performance, especially sprint racing.

According to the invention there is provided a method for predicting the athletic performance potential of a subject comprising the step of assaying a biological sample from a subject for the presence of a polymorphism in the MSTN gene and/or flanking sequences. The polymorphism may be an insertion polymorphism.

The polymorphism may be Chr18g.66495327Ins227 bp66495326. The presence of the Ins227 bp allele is indicative of elite athletic performance. The presence of a homozygous Ins227 bp genotype may indicative of elite athletic performance. The elite athletic performance may be elite sprinting performance. The elite athletic performance may be early two-year old performance.

The biological sample of the subject may be selected from the group comprising: blood, saliva, skeletal muscle, skin, semen, biopsy, bone marrow, soft tissue, internal organs and hair.

The subject may be from a competitive racing species. The subject may be an equine such as a Thoroughbred race horse, Standardbred Trotter, French Trotter or Quarter Horse.

The invention further provides an assay for determining the athletic performance potential of a subject comprising the steps of:
  obtaining a sample;
  extracting or releasing DNA from the sample; and
  identifying a polymorphism (SNP or insertion) in a target sequence from an MSTN gene associated with athletic performance in the extracted or released DNA
wherein the athletic performance potential of a subject is associated with the polymorphism.

The polymorphism may be an insertion polymorphism.
The assay may comprise the step of:
  amplifying a target sequence from a gene or upstream region of a gene associated with athletic performance in the extracted or released DNA
prior to the step of identifying a DNA polymorphism.

The DNA may be genomic DNA

The invention further provides an assay for use in determining the athletic performance potential of a subject comprising means for detecting the presence of a polymorphism (SNP or insertion) in the MSTN gene and/or flanking sequences.

The polymorphism may be Chr18g.66495327Ins227 bp66495326. The presence of a Ins227 bp allele is indicative of elite athletic performance. The presence of a homozygous Ins227 bp genotype may indicative of elite athletic performance. The elite athletic performance may be elite sprinting performance. The elite athletic performance may be early two-year old performance The invention also provides an assay for determining the athletic potential of a subject comprising the step of:
  obtaining a sample;
  extracting or releasing DNA from the sample;
  identifying the genotype of the Chr18g.66495327Ins227 bp66495326 polymorphism in the extracted or released DNA
wherein the presence of a Ins227 bp allele in the Chr18g.66495327Ins227 bp66495326 polymorphism is indicative of elite athletic performance.

The assay may comprise the step of:
  amplifying a target sequence encoding the Chr18g.66495327Ins227 bp66495326 polymorphism in the extracted or released DNA
prior to the step of identifying the genotype of the Chr18g.66495327Ins227 bp66495326 polymorphism.

The presence of a homozygous Ins227 bp genotype indicative of elite athletic performance. The elite athletic performance may be elite sprinting performance.

The DNA may be genomic DNA.
The sample from the subject may be selected from the group comprising: blood, saliva, skeletal muscle skin, bone marrow, biopsy, soft tissue, semen, internal organ and hair.

The subject may be from a competitive racing species. The subject may be an equine such as a Thoroughbred race horse.

BRIEF DESCRIPTION OF THE DRAWINGS

The invention will be more clearly understood from the following description of an embodiment thereof, given by way of example only, with reference to the accompanying drawings, in which:—

DETAILED DESCRIPTION

Figure 1:
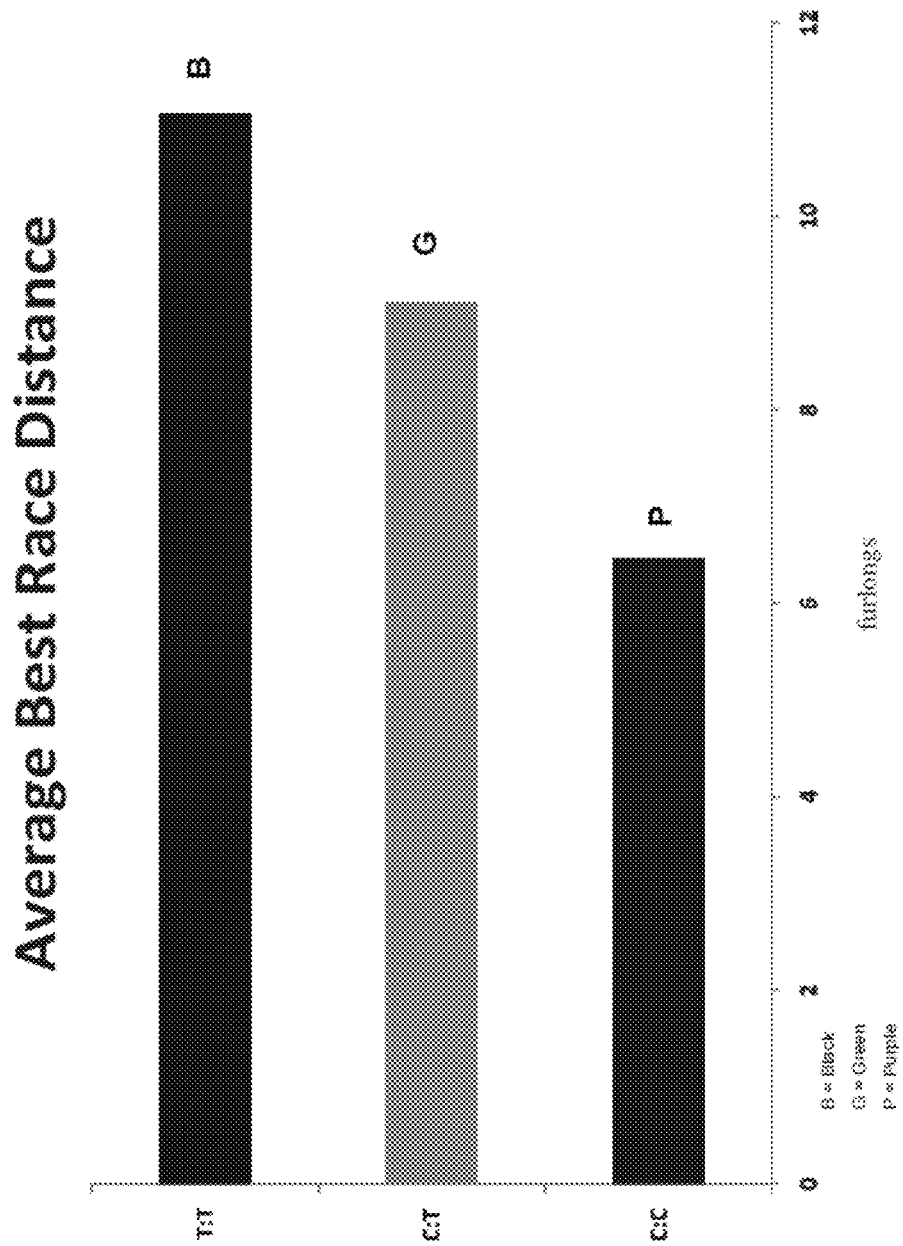
FIG. 1 is a schematic of the best race distance for each of the three MSTN 66493737 (T/C) SNP genotypes.

Intense selection for elite racing performance in the Thoroughbred horse (*Equus caballus*) has resulted in a number of adaptive physiological phenotypes relevant to exercise, however the underlying molecular mechanisms responsible for these characteristics are not well understood.

Thoroughbred horses have been selected for structural and functional variation contributing to speed and stamina during the three century development of the breed. The International Federation of Horseracing Authorities recognizes five distance categories: Sprint (5-6.5 furlongs [f], ≤1,300 m), Mile (6.51-9.49 f, 1,301-1,900 m), Intermediate (9.5-10.5 f, 1,901-2,112 m), Long (10.51-13.5 f, 2,114-2,716 m) and Extended (>13.51 f, >2,717 m) races (www.horseracingintfed.com) and it is widely recognized among horse breeders that variation in physical and physiological characteristics are responsible for variation in individual aptitude for race distance (Willett 1981). Although environment and training may contribute to the race distance for which a horse is best suited, the genetic contribution to the ability to perform optimally at certain distances is large; the heritability of best distance among Australian racehorses has been estimated as 0.94±0.03 (Williamson & Beilharz 1998).

A principal characteristic contributing to the ability of a Thoroughbred to perform well in short distance, sprint races is the extent and maturity of the skeletal musculature. Sprinters are generally shorter, stockier animals with greater muscle mass than animals suited to endurance performance, and generally mature earlier. Performance aptitude for speed and stamina has also been associated with muscle fibre type phenotypes (Rivero et al. 1993; Barrey et al. 1999) and metabolic adaptations to training (Rivero & Piercy 2008). Variation in cardiovascular function contributing to aerobic capacity may also play a role in distinguishing individuals suited to shorter or longer distance races.

We have previously reported a sequence polymorphism (g.66493737C>T) in the equine myostatin (MSTN) gene strongly associated (P=4.85×10$^{-8}$) with optimum racing distance in Thoroughbred racehorses (Hill et al. 2010, the entire contents of which is incorporated herein by reference). In several mammalian species, including cattle, sheep, dogs and horses, muscle hypertrophy phenotypes are associated with sequence variants in the MSTN gene (Grobet et al. 1997; McPherson et al. 1997; McPherron & Lee 1997; Schuelke et al. 2004; Mosher et al. 2007). Among horses that compete preferably in short distance (≤7 f) races requiring exceptional speed, the C allele OF G.66493737 C>T is twice as common than among horses that perform optimally in longer distance (>8 f) races that require more stamina (0.72 and 0.36 respectively). On average the optimum racing distance for C:C horses was 6.2±0.8 f, for C:T horses was 9.1±2.4 f and for T:T horses was 10.5±2.7 f. Furthermore, C:C horses have significantly greater muscle mass than T:T horses at two-years-old.

Skeletal muscle phenotypes clearly play a role in distinguishing distance aptitude, and there is a strong effect of MSTN genotype on distance (Hill et al. 2010, the entire contents of which is incorporated herein by reference). However, heretofore, the effects of additional nuclear gene variants that may contribute to equine performance-related phenotypes have not been investigated. Therefore, we performed a genome-wide SNP-association study using the EquineSNP50 Bead Chip genotyping array in a cohort of elite race winning Thoroughbred horses Animals were separated into two distinct phenotypic cohorts comprising short distance (≤8 f) and middle-long distance (>8 f) race winners and genetic associations were evaluated using best race distance as a quantitative phenotype. This study was designed to identify additional genetic loci as indicators of race distance aptitude and to establish whether variation at the g.66493737C>T SNP was associated with inter-locus epistatic effects for race distance performance.

The present invention relates to a previously unknown relationship between sequence variants (such as SNPs and insertion polymorphism) in the MSTN gene and retrospective athletic performance (given as racecourse success i.e. Group winner or non-winner, handicap rating (RPR) and best race distance for Group winners) in Thoroughbred race horses. In some aspects, the invention relates to sequence variants in the MSTN gene and flanking sequences. In some aspects the invention relates to sequence variants in linkage disequilibrium with sequence variants in the MSTN gene.

MSTN

Myostatin is also known as growth/differentiation factor 8 precursor (GDF-8). In several mammalian species (including cattle, sheep and dogs), the double muscling trait is caused by mutations in the myostatin (MSTN) gene. In dogs, MSTN gene mutations in racing whippets have been associated with the 'bully' phenotype and heterozygous individuals are significantly faster than individuals carrying the wild-type genotype (Mosher et al 2007). Mutations in the MSTN gene may be associated with athletic power.

We have analysed a number of polymorphisms (including SNPs and insertion polymorphisms) in the MSTN gene for association with athletic performance and have developed a simple DNA based method of predicting the athletic performance potential of a subject based on the novel polymorphisms.

A genome-wide SNP-association study for optimum racing distance was performed using the EquineSNP50 Bead Chip genotyping array in a cohort of n=118 elite Thoroughbred racehorses divergent for race distance aptitude. In a cohort-based association test we evaluated genotypic variation at 40,977 SNPs between horses suited to short distance (≤8 f) and middle-long distance (>8 f) races. The most significant SNP was located on chromosome 18: BIEC2-417495 ~690 kb from the gene encoding myostatin (MSTN) [$P_{unadj.}$=6.96×10$^{-6}$]. Considering best race distance as a quantitative phenotype, a peak of association on chromosome 18 (chr18:65809482-67545806) comprising eight SNPs encompassing a 1.7 Mb region was observed. Again, similar to the cohort-based analysis, the most significant SNP was BIEC2-417495 ($P_{unadj.}$=1.61×10$^{-9}$; $P_{Bonf.}$=6.58×10$^{-5}$). In a candidate gene study we have previously reported a SNP (g.66493737C>T) in MSTN associated with best race distance in Thoroughbreds; however, its functional and genome-wide relevance were uncertain. Additional re-sequencing in the flanking regions of the MSTN gene revealed four novel 3' UTR SNPs and a 227 bp SINE insertion polymorphism in the 5' UTR promoter sequence. Linkage disequilibrium was highest between g.66493737C>T and BIEC2-417495 ($r^2$=0.86).

Comparative association tests consistently demonstrated the g.66493737C>T SNP as the superior variant in the prediction of distance aptitude in racehorses (g.66493737C>T, P=1.02×10$^{-10}$; BIEC2-417495, $P_{unadj.}$=1.61×10$^{-9}$). Functional investigations will be required to determine whether this polymorphism affects putative transcription-factor binding and gives rise to variation in gene and protein expression. Nonetheless, these data demonstrate that the g.66493737C>T SNP provides the most powerful genetic marker for prediction of race distance aptitude in Thoroughbreds.

The invention will be more clearly understood from the following examples.

EXAMPLES

Materials and Methods

Subjects

A Thoroughbred is a registered racehorse that can trace its ancestry to one of three foundation stallions and the approximately 30 foundation mares entered in The General Studbook, 1791 (Weatherby and Sons 1791). There are two types of Thoroughbred race: National Hunt races are run over hurdles or steeplechase fences over distances of up to 4.5 miles (7,200 m), while Flat races have no obstacles and are run over distances ranging from five furlongs (⅝ mile or 1,006 m) to 20 furlongs (4,024 m). The highest standard and most valuable elite Flat races are known as Group (Europe and Australasia) or Stakes races (North America). The most prestigious of these races include The Breeders' Cup races (United States), The Kentucky Derby (United States), The Epsom Derby (United Kingdom) et cetera.

Three hundred and fifty Group races are run in Europe (Britain, Ireland (incl. Northern Ireland), France, Germany, Italy) annually including 84 Group 1, 93 Group 2 and 173 Group 3 races. In the United Kingdom and Ireland 196 Group races are competed annually (43 Group 1, 50 Group 2 and 103 Group 3). Britain has the highest number of Group races (139) in Europe per annum, with 57% run over distances≤1 mile (1609 meters) and 43% run over distances>1 mile. Australia has approximately 540-550 Group races per season from a total of almost 21,000 races and New Zealand hosts 78 Group races per season. After Group races, Listed races are the next highest grade of race.

Horses that compete over distances≤1 mile are known as 'sprinters' whereas horses that compete over distances>1 mile are known as 'stayers'. Horses competing in 1 mile races ('milers' and 'middle distance') may be considered either sprinters or stayers and the way in which a race is executed by the rider often reflects the trainers perceived ability ('sprinter' or 'stayer') of the horse. The International Federation of Horseracing Authorities recognizes five race distance categories: Sprint (5-6.5 f, ≤1,300 m), Mile (6.51-9.49 f, 1,301-1,900 m), Intermediate (9.5-10.5 f, 1,901-2,112 m), Long (10.51-13.5 f, 2,114-2,716 m) and Extended (>13.51 f, >2,717 m); S-M-I-L-E [Note: 1 furlong=⅛ mile=201.2 meters].

A repository of registered Thoroughbred horse blood or hair samples (n>1,400) was collected from stud farms, racing yards and sales establishments in Ireland, Great Britain and New Zealand during 1997 to 2008. Each sample was categorized based on retrospective racecourse performance records. Only horses with performance records in Flat races were included in the study. The study cohort comprised elite Thoroughbreds that had won at least one Group race (Group 1, Group 2 or Group 3) or a Listed race—the highest standard and most valuable elite Flat races are known as Group (Stakes) races and Listed races are the next in status. Only elite race winning horses were included as elite races are most likely to reflect the truest test for distance. Race records were derived from three sources [Europe race records: The Racing Post on-line database (www.racingpost.co.uk); Australasia and South East Asia race records: Anion Pedigrees (www.arion co.nz); North America race records: Pedigree Online Thoroughbred database (www.pedigreequery.com)].

Each sample was assigned a best race distance which was defined as the distance (furlongs, f) of the highest grade of race won [note: 1 furlong=⅛ mile=201.2 meters]. When multiple races of the same grade were won, then the distance of the most valuable race, in terms of prize money, was used. A set of elite Thoroughbred samples (n=118) was selected from the repository, mostly comprising samples procured in Ireland and Great Britain (i.e. n=5 samples [n=3≤8 f, n=2>8 f] were collected in New Zealand); though some had won their best race in North America. Animals with excessive consanguinity (within two generations) were avoided and over-representation of popular sires within the pedigrees was minimized as far as possible. One hundred and seven sires were represented in the total sample set.

For the case-control investigation we compared two cohorts: samples were subdivided into short (≤8 f, n=68) and middle-long (>8 f, n=50) distance elite race winning cohorts (Table 1 below).

TABLE 1

Description of phenotype cohorts

| | N | No. sires | Mean RPR | Range RPR | Mean BRD | Range BRD |
|---|---|---|---|---|---|---|
| All TBs | 118 | 107 | 116 | 84-138 | 8.6 | 5-16 |
| Short (≤8 f) | 68 | 63 | 114 | 84-129 | 6.8 | 5-8 |
| Middle-long (>8 f) | 50 | 48 | 120 | 107-138 | 11.3 | 9-16 |

All TBs (Thoroughbreds) were used for the quantitative association test analysis. Racing Post Ratings (RPR) represent handicap ratings (best lifetime RPR) that are indicative of performance ability. Best race distance (BRD) was the distance (f) of the highest grade of race (Group 1, 2, 3, Listed) won.

DNA Extraction

Genomic DNA was extracted from either fresh whole blood or hair samples using a modified version of a standard phenol/chloroform method (Sambrook & Russell 2001) or the Maxwell 16 automated DNA purification system (Promega, Wis., USA). DNA samples were quantified using Quant-iT PicoGreen dsDNA kits (Invitrogen, Carlsbad, Calif.) according to the manufactures instructions and the DNA concentrations were adjusted to 20 ng/µl.

Detection of Polymorphism

The sequence variant may be determined by any genotyping method including for example the following non limiting methods: direct DNA sequencing; allele size discrimination using gel based assays; single-strand conformation polymorphisms; high-resolution melting of PCR amplicons; matrix-assisted laser-desorption-ionization mass spectrometry.

Genotyping and Quality Control

Samples were genotyped using EquineSNP50 Genotyping BeadChips (Illumina, San Diego, Calif.). This array contains approximately 54,000 SNPs ascertained from the EquCab2 SNP database of the horse genome (Wade et al. 2009) and has an average density of one SNP per 43.2 kb. Genotyping was performed by AROS Applied Biotechnology AS, Denmark. The samples that were genotyped for this study were a subset of n=187 samples genotyped in two separate batches (Batch 1, n=96; Batch 2, n=91). We included four pairs of duplicate samples in Batch 2 for QC purposes and observed greater than 99.9% concordance in the four pairs. In total, we successfully genotyped 53,795 loci. All samples had a genotyping rate of greater than 90%. We omitted SNPs which had a genotyping completion rate of less than 90%, were monomorphic or had minor allele frequencies (MAF) less than 5% in our samples from further analysis. We omitted 12,818 SNPs leaving 40,977 SNPs in our working build of the data and the overall genotype completion rate was 99.8%.

Re-Sequencing MSTN Flanking Sequences

PCR primers were designed to cover ~2 kb of the 5'UTR and ~2 kb of the 3' UTR of MSTN genomic sequence using the PCR Suite extension to the Primer3 web-based primer design tool (Rozen & Skaletsky 2000; van Baren & Heutink 2004) (Table 2 below). Fifteen unrelated Thoroughbred DNA samples (g.66493737C>T, n=5 C:C; n=5 C:T, n=5 T:T) were included in a re-sequencing panel to identify novel sequence variants. Bidirectional DNA sequencing of PCR products was performed by Macrogen Inc. (Seoul, Korea) using AB 3730x1 sequencers (Applied Biosystems, Foster City, Calif.).

Sequence variants were detected by visual examination of sequences following alignment using Consed version 19.0 (Gordon et al. 1998).

The following primers were used: forward 5'-ATCAGCT-CACCCTTGACTGTAAC-3'(SEQ ID No. 17) and reverse 5'-TCATCTCTCTGGACATCGTACTG-3' (SEQ ID No. 18).

TABLE 2

PCR and sequencing primers for re-sequencing MSTN flanking sequences

| Oligonucleotide Name | Oligonucleotide Primer Sequence 5'-3' | SEQ ID No | Structure |
|---|---|---|---|
| Forward and reverse primers for MSTN 3' UTR PCR and sequencing | | | |
| PCR Primer 3'UTR (Forward) | TACTCCCACAAAGATGTCTCCAAT | 1 | |
| PCR Primer 3'UTR (Reverse) | TGAATCACCTCCTGCATTAGACT | 2 | |
| Sequencing Primer 1 3'UTR (Forward) | GAATGGCTGATGTCATCAGG | 3 | |
| Sequencing Primer 1 3'UTR (Reverse) | CCTGATGACATCAGCCATTC | 4 | |
| Sequencing Primer 2 3'UTR (Forward) | CAAATCTCAACGTTCCATTG | 5 | |
| Sequencing Primer 2 3'UTR (Reverse) | CAATGGAACGTTGAGATTTG | 6 | |
| Forward and reverse primers for MSTN 5' UTR PCR and sequencing | | | |
| PCR Primer 5'UTR (Forward) | CTGGTTTGTGTCTGGTTTTC | 7 | |
| PCR Primer 5'UTR (Reverse) | CTTTTCCTTCCTGCTTACATAC | 8 | |
| Sequencing Primer 1 5'UTR (Forward) | AACAAAACAAACAGGCACCC | 9 | 5' upstream |
| Sequencing Primer 1 5'UTR (Reverse) | GGGTGCCTGTTTGTTTTGTT | 10 | 5' upstream |
| Sequencing Primer 2 5'UTR (Forward) | GTCAGGAAAACAAGTTTCTCAAA | 11 | 5' upstream |
| Sequencing Primer 2 5'UTR (Reverse) | TTTGAGAAACTTGTTTTCCTGAC | 12 | 5' upstream |
| Sequencing Primer 3 5'UTR (Forward) | GACAGCGAGATTCATTGTGG | 13 | 5' upstream + part Exon 1 |
| Sequencing Primer 3 5'UTR (Reverse) | CCACAATGAATCTCGCTGTC | 14 | 5' upstream + part Exon 1 |
| Sequencing Primer 4 5'UTR (Forward) | CCTGTTTGTGCTGATTCTTG | 15 | 5' upstream + part Exon 1 |
| Sequencing Primer 4 5'UTR (Reverse) | CAAGAATCAGCACAAACAGG | 16 | 5' upstream + part Exon 1 |

Bioinformatics

The software tool MatInspector (Cartharius et al. 2005) was used to search for transcription factor binding site consensus sequences present in 300 bp of the MSTN 5' UTR region in which a novel SINE insertion (Ins227 bp) polymorphism was detected. To investigate possible microRNA (miRNA) regulation of MSTN gene expression we screened the equine MSTN gene and flanking sequences for putative miRNA binding sites. A list of 407 predicted equine miRNAs (Zhou et al. 2009) were inputted into the online tool DIANA microtest (http://diana.pcbi.upenn.edu/cgi-bin/micro_t.cgi) and a 14.7 kb segment containing the equine MSTN gene and ~5 kb of upstream and downstream sequence was inputted as the target sequence. SNPInspector (Cartharius et al. 2005) was used to investigate transcription factor binding sites at the g.66493737C>T locus.

Genotyping the Chr18g.66495327Ins227 bp66495326 (Ins227 bp) Polymorphism

A PCR-based assay for allele size discrimination was used to genotype the Ins227 bp polymorphism in n=165 samples. Alleles were determined as follows: Normal allele –600 bp; and Insertion227 bp allele –827 bp.

Statistical Analyses

All statistical analyses, including tests of association were performed using PLINK Version 1.05 (Purcell et al. 2007). We compared genotype frequencies in short and middle-long distance cohorts, testing for trait association using $\chi^2$ tests with two degrees of freedom. To test for population stratification, the pairwise identity-by-state (IBS) distance was calculated for all individuals. A permutation test was performed to investigate IBS differences among the short and middle-long distance cohorts. The linear regression model was used to evaluate quantitative trait association using best race distance (f) as the phenotype. We report uncorrected P-values ($P_{unadj}$) and P-values following correction for multiple testing using the Bonferroni method ($P_{Bonf}$). Manhattan and Q-Q plots were generated in R using a modified version of code. The regional association plot was generated in R using a modified version of code available at http://www.broadinstitute.org.

Cohort-based association (short vs middle-long distance) and quantitative trait association tests were also performed for the g.66493737C>T SNP (Hill et al. 2010) and a novel 5'UTR MSTN SINE insertion (Ins227 bp) polymorphism identified in this study. In addition, an analysis of genome-wide epistasis was performed in which the g.66493737C>T SNP was tested against all SNPs on the EquineSNP50 Genotyping BeadChip for epistatic interactions influencing best race distance. This test involved a linear regression analysis to investigate whether gene by gene interactions had a significant influence on best race distance. Linkage disequilibrium (LD) between g.66493737C>T and Ins227 bp and between g.66493737C>T and all chromosome 18 SNPs on the EquineSNP50 Genotyping BeadChip was quantified as $r^2$. A visual representation of haplotype blocks across a 1.7 Mb region on chromosome 18 was generated using Haploview (FIG. 6) (Barrett et al. 2005; Barrett 2009).

Ethics

This work has been approved by the University College Dublin, Ireland, Animal Research Ethics Committee.

Example 1

Genome-Wide SNP-Association Study & Candidate Performance-Associated Genes

Genome-Wide SNP-Association Study

We have previously described an association between optimum racing distance and a SNP (g.66493737C>T) in the equine MSTN gene in Thoroughbred Flat racehorses (Hill et al. 2010, the entire contents of which is incorporated herein by reference). Candidate gene approaches are designed considering a priori hypotheses and do not allow the opportunity for evaluation of the effect of the gene in the context of the entire genome, nor do they allow for the identification of other genes contributing to the phenotype (Tabor et al. 2002; Jorgensen et al. 2009). Therefore, employing a hypothesis-free approach we investigated genome-wide influences on optimum racing distance by conducting a genome-wide SNP-association study in a cohort of elite Thoroughbred racehorses.

Figure 3:
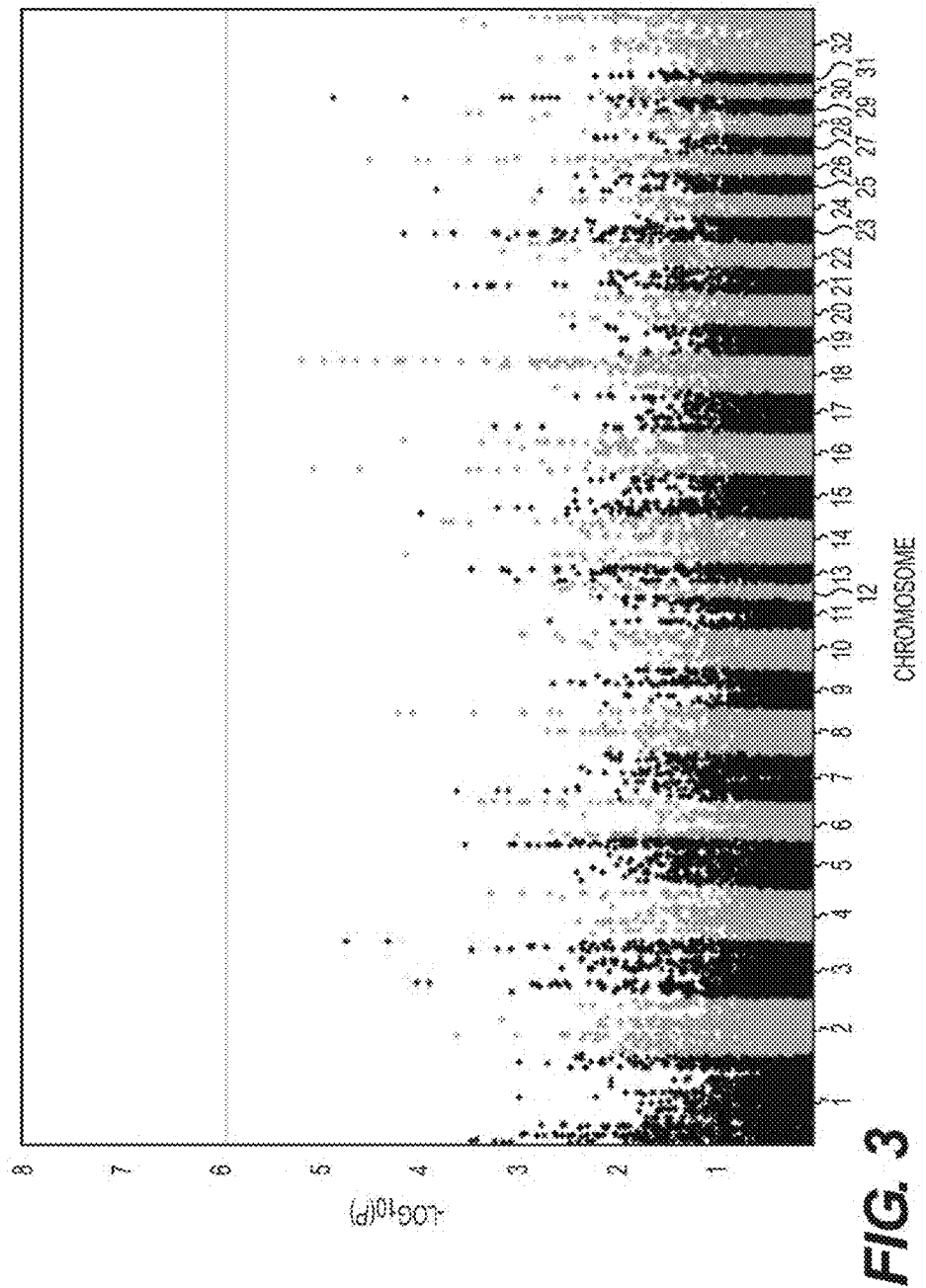
FIG. 3 is a Manhattan plot of P-value for genotype-phenotype GWAS in short (≤8 f) and middle-long (>8 f) distance elite race winners. The y-axis plots $-\log_{10}$(P-values) and the x-axis plots the physical position of the SNPs sorted by chromosome and chromosome position. The most significant SNP was on chromosome 18 (BIEC2-417495). No SNP remained statistically significant following correction for multiple-testing.

In a cohort-based genotype-phenotype investigation we compared two cohorts: short (≤8 f) and middle-long (>8 f) distance elite race winners. The genome-wide association study (GWAS) results, sorted by chromosome, are shown in FIG. 3. The most significant SNP was on chromosome 18 (BIEC2-417495, $P_{unadj.}=6.96\times10^{-6}$) and five of the top ten SNPs were located together spanning a 2.4 Mb region on chromosome 18 (chr18:64725066-67186093). However, no SNP in this analysis reached genome-wide significance following correction for multiple-testing.

The SNPs identified in chromosome 18 during the horse genome sequencing project and those that are found on the EquineSNP50 BeadChip can be viewed at http://www.broadinstitute.org/ftp/distribution/horse_snpSer. No. release/v2/(fileequcab2.0_chr18_snps.xls), the entire contents of which is incorporated herein by reference. Pairwise IBS values were used to investigate population stratification between the short and middle-long cohorts. While on average phenotypically concordant pairs of individuals were more similar than phenotypically discordant pairs (P=0.034), the overall difference between the two groups was negligible (<0.0002).

Figure 4:
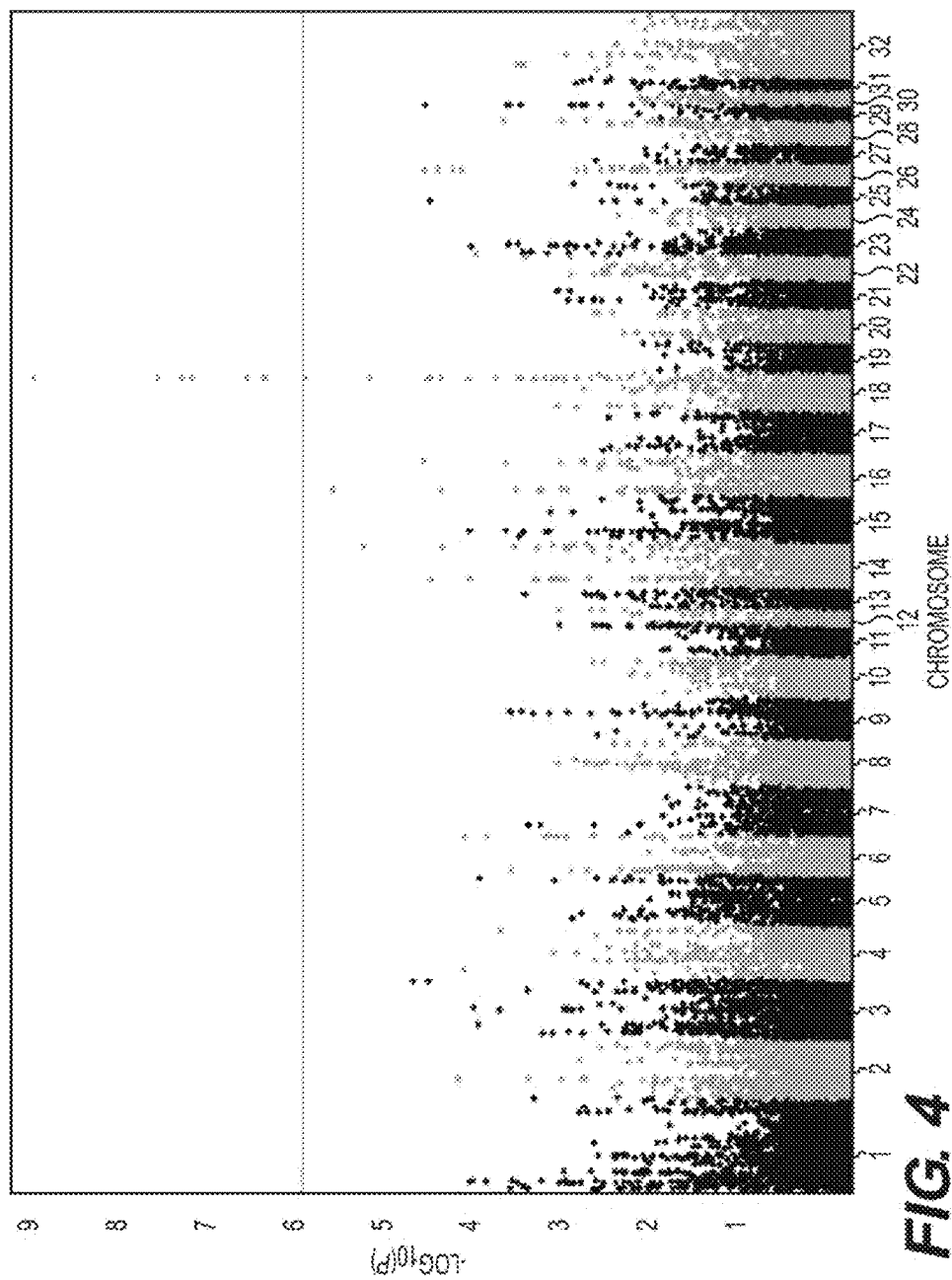
FIG. 4 is a Manhattan plot of P-value for quantitative trait GWAS using best race distance as phenotype. The y-axis plots $-\log_{10}$(P-values) and the x-axis plots the physical position of the SNPs sorted by chromosome and chromosome position. A peak of association on chromosome 18 (chr18: 65809482-67545806) encompassed a ~1.7 Mb region (shown in FIG. 5). Seven of the chromosome 18 SNPs remained significant following correction for multiple testing. The most significant SNP was BIEC2-417495 ($P_{Bonf.}$=6.58× $10^{-5}$)
Figure 5:
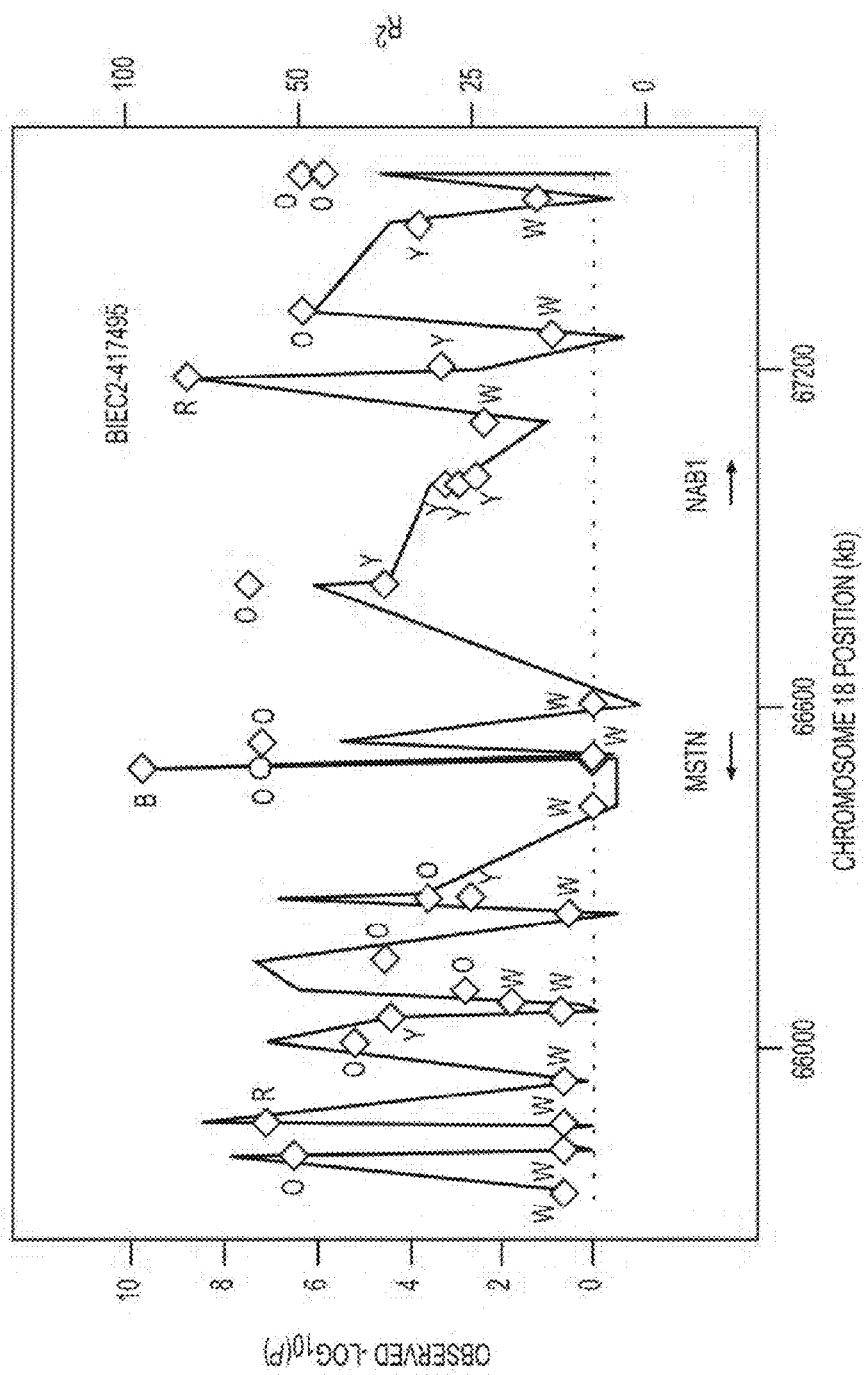
FIG. 5 is a regional plot for the 1.8 Mb peak of association on chromosome 18 containing the MSTN and NAB1 genes. Association plot of the 1.8 Mb region encompassing 40 SNPs (diamonds) and the Ins227 bp polymorphism (circle) ranging from one SNP upstream and one SNP downstream of the seven SNPs significantly associated with optimum racing distance following correction for multiple testing. The y-axes plot $-\log_{10}$(P-values) for each SNP (diamonds) and $r^2$ (blue line (solid line)) between g.66493737C>T and all other SNPs. The x-axis plots the physical position of each SNP in the region. The best SNP, g.66493737C>T, is indicated with a blue diamond (indicated with B). Each SNP is color coded according to the strength of LD with g.66493737C>T: $r^2 \geq 0.8$, red (indicated with R); $r^2 \geq 0.5 < 0.8$, orange (indicated with O); $r^2 \geq 0.2 < 0.5$, yellow (indicated with Y); $r^2 < 0.2$, white (indicated with W)

Using the linear regression model, we considered best race distance as a quantitative phenotype and observed the same peak of association on chromosome 18 (chr18:65809482-67545806) (FIG. 4). The unadjusted and FDR corrected P values for quantitative association test result for best race distance are given in additional file 1 which can be downloaded at http://www.biomedcentral.com/1471-2164/11/552, the entire contents of which are incorporated herein by reference. The top eight SNPs encompassed a 1.7 Mb region on chromosome 18 (FIG. 5) and seven reached genome-wide significance following correction for multiple testing ($P_{Bonf.}<0.05$). The most significant SNP was also the most significant in the cohort-based analysis: BIEC2-417495 ($P_{unadj.}=1.61\times10^{-9}$; $P_{Bonf.}=6.58\times10^{-5}$).

Candidate Performance-Associated Genes

We investigated candidate genes in the 1.7 Mb (Chr18: 65809482-67545806) region on chromosome 18 that encompassed the seven SNPs that reached genome-wide significance. Eleven protein coding genes were identified, including the myostatin gene (MSTN) and the NGFI-A binding protein 1 (EGR1 binding protein 1) gene (NAB1).

The genomic region on chromosome 18 containing the MSTN gene was the highest ranked region in the GWAS for best racing distance, reaching genome-wide significance for a set of seven SNPs within a 1.7 Mb region. The best SNP (BIEC2-417495) and the second best SNP (BIEC2-417372) were 692 kb and 28 kb from the MSTN gene, respectively. We searched the region for other plausible candidate genes and identified the NGFI-A binding protein 1 (EGR1 binding protein 1) gene (NAB1) located ~170 kb from BIEC2-417495. The product of the NAB1 gene is highly expressed in cardiac muscle and has been reported to be a transcriptional regulator of cardiac growth (Buitrago et al. 2005). Its principal role is in its interaction with the early growth response 1 (EGR-1) transcriptional activator that is involved in regulation of cellular growth and differentiation (Thiel et al. 2000).

We considered NAB1 as a strong candidate gene to influence an athletic performance phenotype as we have previously identified EGR-1 mRNA transcript alterations (+1.6-fold, P=0.014) in skeletal muscle immediately following a bout of treadmill exercise in untrained Thoroughbred horses (McGivney et al. 2009). Twelve SNPs located within the NAB1 genomic sequence (chr18:g.66995249-67021729) are documented in the EquCab2 SNP database, and three are contained on the EquineSNP50 Genotyping BeadChip. After correction for multiple testing, there were no detectable associations between the three NAB1 SNPs and the trait (BIEC2-417453, $P_{unadj.}=0.0007$, rank 144; BIEC2-417454, $P_{unadj.}=0.0012$, rank 210; and BIEC2-417458, $P_{unadj.}=0.0032$, rank 421). Therefore, we did not further consider NAB1 as a potential major contributor to variation in optimum racing distance.

Example 2

Polymorphism Detection in Equine MSTN Flanking Sequences

We have previously identified SNPs in intron 1 of the equine MSTN gene by re-sequencing the coding and intronic sequence [PCT/IE2009/000062 and Hill et al. 2010, the entire contents of which are incorporated herein by reference]. Details of two of the SNPs identified in Intron 1 are shown in Table 3 below.

TABLE 3

SNPs in intron 1 of the MSTN gene

| SNP ID | Location (bp) on ECA 18 SNP (EquCab2) | Structure | Flanking Sequence |
|---|---|---|---|
| MSTN_66493737 (T/C) SNP | T:C 66493737 | Intron 1 | AGCTAAGCAAGTAATTAGCACAAAAA TTTGAATGTTATATTCAGGCTATCTCA AAAGTTAGAAAATACTGTCTTTAGAGC CAGGCTGTCATTGTGAGCAAAATCACT AGCAATTTCTTTTATTTTGGTTCCCCAA GATTGTTTATAAATAAGGTAAATCTAC TCCAGGACTATTTGATAGCAGAGTCAT AAAGGAAAATTA[T/C]TTGGTGCATTA TAACCTGATTACTTAATAAGGAGAAC AATATTTTGAAACTGTTGTGTCCTGTT TAAAGTAGATAAAGCACTGGGTAAAG CAGGATCGCAGACACATGGCACAGAA TCTTCCGTGTCATGCCTTCTCTGTGAA GGTGTCTGTCTCCCTTTCCTTGAGTGT AGTTATGAACTGACTGCAAAAAGAAT ATATG (SEQ ID No. 19) |
| MSTN_66494218 (A/C) SNP | A:C 66494218 | Intron 1 | AGGAGATTATTAAGCAATGTGCCTGCC TGGAAATGTGCACCCCGGGTGCTCTCA ACAATAGTACTATGGTCAAGGTGTAA GCAGGACTCTGAGCTATAACCTCTTTG ATTAAAATGTTTATTTATTAGGCATTT TATGATAATTAGCTCATGATTATCATT ATGCTATGTTTACTTCATCATTTTTCTT ACTAATACATTA[A/C]ATTTTAAAAAA TATTTTTCTAATCTCCAGGGGAATAAC TTTCAAAATCTAATATGTTAATTTGTG AAGAACATAAAAACACTATGAGAAAT AGTTTTGAGTAACAGAAGTCATTTTGG TGTTCAGCAAATGCTCAAATGACCTAA ACGTCTACAAATTTCTTCCTTCTCTATT ATTAGTGAAAAAAACTTGTTATTATAA (SEQ ID No. 20) |

Details of two SNPs in the genomic region on chromosome 18 containing the MSTN gene that ranked highly in the GWAS for best racing distance are shown in Table 4 below.

TABLE 4

SNPs from Equine SNP50 Genotyping Bead Chips that ranked highly in the GWAS for best racing distance.

| SNP ID | Location (bp) on ECA 18 SNP (EquCab2) | Structure | Flanking Sequence |
|---|---|---|---|
| BIEC2-417495 | C:T 67186093 | Intergenic | CATAAGGTCAAATATTTTTCCCATTTCCCTCTTTTATTA AAATACCACATTTATTTGGAAAATCATTACTCAGCTCT ATTGCTTACTAATTATTTTAAGATAGAAAAAATATTTT GTCGCAAAGAAAGATTTCAAGACATCTTTATGGCTAT ATAAATATTTATGCATCTTTTTAAATACCTTGATTGAT TGGTTTTAGA[C/T]TGTCTCAGATTCCATCTGATTTCTC TGCCTCCCTGATAAACCTTCTTCAATCTCTGTTCCCTGG CCTATGAAGGTCACCTTCAAAATATTATCACCTTTATGT AATGATCAGACACAAAGTCTAACCATCATCTAAATTATT TCAATATGAAGCATGACTAATAAACCAGTATGAGTAGT TTTCAAAGTGAACAGGATTT (SEQ ID No. 21) |
| BIEC2-417372 | A:G 66539967 | Intergenic | GCCTGGATATGAAGCCCATAAGAAATGTCTGGCAGTG GTCTCTTGAGATCAGAAAGAGAATGGGAGATTAGGAA GTTAGAATAGGAAGCAAGTGAGGCAGCAGGTAGYGG AGGCTAGGTGGCCCATCTGTGAGTTTTTTCCTTCTGAA CTCCTTACAATTCTTTATAAAATTCCATGAAGGCCTCA TTTCAAGATAAAGG[G/A]GAAGAAAATATTTTCTCCTA AAAAAGCTTAAACTTAATATTCTACTTCTCAAAAAAAA |

TABLE 4-continued

SNPs from Equine SNP50 Genotyping Bead Chips that ranked highly in the GWAS for best racing distance.

| SNP ID | SNP | Location (bp) on ECA 18 (EquCab2) | Structure | Flanking Sequence |
|---|---|---|---|---|
| | | | | TTCAAAGAGGCCTAATAGATTGACTGGAACTCTAACTG AAATTTGCCTCGCTTTCCCAAATTCTTACTGGAGAAGGG CAAGGCCTCGCCCCTCTCAGAACTCTTACATGAGATTGC TGCTTTCCTTAGTTTCTGATCACTGT (SEQ ID No. 22) |

The structure of the MSTN gene is predicted as follows (Ensembl data) (Table 5)

TABLE 5

Structure of the MSTN gene

| | Start bp | End bp | Length bp |
|---|---|---|---|
| 5' upstream | | 66,495,181 | |
| Exon 1 | 66,494,808 | 66,495,180 | 373 |
| Intron 1 | 66,492,979 | 66,494,807 | 1829 |
| Exon 2 | 66,492,605 | 66,492,978 | 374 |
| Intron 2 | 66,490,589 | 66,492,604 | 2016 |
| Exon 3 | 66,490,208 | 66,490,588 | 381 |
| 3' downstream | 66,490,207 | | |

We re-sequenced 2,155 bp (chri8:66488052-66490207) of the 3'UTR sequence of MSTN sequence of the equine myostatin (MSTN) gene in 15 unrelated Thoroughbred horses and identified 4 novel SNPs. (Table 6)

TABLE 6

SNPs identified in 3' UTR sequence of MSTN

| SNP ID | SNP | Location in Contig (full length 2139 bp) bp | Location (in the downstream of the protein coding region of MSTN) bp | Location on ECA18 (EquCab2) bp | Structure |
|---|---|---|---|---|---|
| SNP1 | A:C | 701 | 595 | 66,489,613 | 3' UTR |
| SNP2 | C:T | 943 | 837 | 66,489,371 | 3' UTR |
| SNP3 | A:G | 954 | 848 | 66,489,360 | 3' UTR |
| SNP4 | A:T | 2001 | 1895 | 66,488,313 | 3' UTR |

Polymorphisms in the 3' UTR of the MSTN gene have been associated with muscle hypertrophy in sheep and are considered likely to function via creation of de novo target sites for the microRNAs (miRNA) miR-1 and miR-206 (Clop et al. 2006). Therefore, using a set of equine miRNAs (n=407) described by Zhou and colleagues (Zhou et al. 2009) we investigated the presence of putative miRNA binding sites within ~5 kb upstream and downstream flanking sequences of the MSTN gene. Five putative miRNA binding sites were identified, though none was polymorphic: i.e. no putative miRNA binding site was associated with any of the eight SNP alleles.

We re-sequenced 2,151 bp (chr18:66494683-66496834) of the 5' UTR sequence of the equine myostatin (MSTN) gene in 15 unrelated Thoroughbred horses.

Re-sequencing was performed using four internal sequencing primers following PCR using the 5' UTR PCR and sequencing primers listed in Table 2 above (SEQ ID No. 7-16).

Following re-sequencing in the 5' UTR of the MSTN gene, we identified a 227 bp insertion polymorphism at chr18: 66495327-[Insertion227 bp]-66495326, located 146 bp from the start of Exon 1 (Exon1Start: 66495180).

The insertion seauence is as follows:

```
                                          (SEQ ID No. 23)
GGGGCTGGCCCCGTGGCCGAGTGGTTAAGTTCGTGCGCTCCGCTGCAGGC

GGCCCAGTGTTTCGTCGGTTCGAGTCCTGGGCGCGGACATGGCACTGCTC

GTCGGACCACGCTGAGGCAGCGTCCCACATGCCACAACTAGAGGAACCCA

CAACGAAGAATACACAACTATGTACCGGGGGGCTTTGGGGAGAAAAAGGA

AAATAAAATCTTTAAAAAGCCACTTGG
```

A BLAST search identified the insertion sequence as a horse-specific repetitive DNA sequence element (SINE) known as ERE-1 (Sakagami et al J. Mol. Biol. 239 (5), 731-735 (1994). Also MatInspector analysis indicated that the insertion may disrupt on E-box motif Summary of Polymorphisms in the MSTN Flaking Region We have identified five polymorphisms in the upstream and downstream untranslated (UTR) regions of the MSTN gene. We have identified four novel SNPs (i.e. not documented in the EquCab2.0 SNP database) and an insertion polymorphism (not previously documented). Details for these polymorphisms are provided in the Table 7 below.

TABLE 7

Details of polymorphisms identified in the MSTN flanking region.

| SNP ID | SNP | Location (bp) on ECA18 (EquCab2) | Structure | Flanking sequences |
|---|---|---|---|---|
| Insertion 227 bp | Insertion 227 bp | 66495327 [Insertion2 27 bp] 66495326 | 5' UTR | TTGTGACAGACAGGGTTTTAACCTCTGACAGCG AGATTCATTGTGGAGCAGGAGCCAATCATAGAT CCTGACGACACTTGTCTCATCAAAGTTGGAATA TAAAAAGCCACTTGG[GGGGCTGGCCCCGTGGC CGAGTGGTTAAGTTCGTGCGCTCCGCTGCAGGC GGCCCAGTGTTTCGTCGGTTCGAGTCCTGGGCG CGGACATGGCACTGCTCGTCGGACCACGCTGAG GCAGCGTCCCACATGCCACAACTAGAGGAACCC ACAACGAAGAATACACAACTATGTACCGGGGG GCTTTGGGGAGAAAAAGGAAAATAAAATCTTTA AAAAGCCACTTGG]AATACAGTATAAAAGATTC ACTGGTGTGGCAAGTTGTCTCTCAGACTGTACA GGCATTAAAATTTTGCTTGGCATTGCTCAAAAG CAAAAGAAAAGTAAAAGGAAGAAATAAGAGCA AGGAAAAAG (SEQ ID No. 38) |
| SNP1 | A:C | 66489613 | 3' UTR | TATATACCATCATTTTGATTATCCTTATACACTT GAATTTATATTGTATAATAGCATACTTGGTAAG ATGAAATTCCACAAAAATAGGAATGGTACACCA TATGCAAGTTTCCATTCCTATTGTGATTGATACA GTACATTAACAATCCACACCAATGGTGCTAATA CAAATAGGCTGAATGGCTGATGTCATCAGGTTT AT[C/A]AAATAAAAACATCCAATAAAATAATGT TTCTCCTTTCTTCAGGTGCATTTTCCAAATGGGG AATGGATTTTCTTTAATGAAAGAAGAATCATTT TTCTAGAGGTCAGGATTTAATTCTGTAGCATACT TGGAGAAACTGCATTACCTTAAAAGGCAGCCAA AAAGTATTCATTTTTATCAAAATTTCAAAATTGC AGCCTGCTTTTGCAACATTGCAGT (SEQ ID No. 24) |
| SNP2 | C:T | 66489371 | 3' UTR | ATCCAATAAAATAATGTTTCTCCTTTCTTCAGGT GCATTTTCCAAATGGGGAATGGATTTTCTTTAAT GAAAGAAGAATCATTTTTCTAGAGGTCAGGATT TAATTCTGTAGCATACTTGGAGAAACTGCATTA CCTTAAAAGGCAGCCAAAAAGTATTCATTTTTA TCAAAATTTCAAAATTGCAGCCTGCTTTTGCAA CATTGCAGTTTTTATGATAAAATAATGGAAA[C/ T]GACTGATTCTGTCAATATTGTATAAAAAGACT TGAGACAATTGCATTTATATAATATGTATACA ATATTGTTTTGTAAATAAGCGTCTCCTTTTTTA TTTACTTTGGTATATTTTTACAGTCAGAACATTT CAAATTAAGTATTAAGGCACAAAGACATGTCAT GTATGACAGAAAAGCAACTGCTTATATTTCGGG GCAAATTAGCAGATTAAATAGTGGTCTTAAAAC TCCATATGCTAATGGTTAGA (SEQ ID No. 25) |
| SNP3 | A:G | 66489360 | 3' UTR | ATCCAATAAAATAATGTTTCTCCTTTCTTCAGGT GCATTTTCCAAATGGGGAATGGATTTTCTTTAAT GAAAGAAGAATCATTTTTCTAGAGGTCAGGATT TAATTCTGTAGCATACTTGGAGAAACTGCATTA CCTTAAAAGGCAGCCAAAAAGTATTCATTTTTA TCAAAATTTCAAAATTGCAGCCTGCTTTTGCAA CATTGCAGTTTTTATGATAAAATAATGGAAATG ACTGATTCT[G/A]TCAATATTGTATAAAAAGACT TGAGACAATTGCATTTATATAATATGTATACA ATATTGTTTTGTAAATAAGCGTCTCCTTTTTTA TTTACTTTGGTATATTTTTACAGTCAGAACATTT CAAATTAAGTATTAAGGCACAAAGACATGTCAT GTATGACAGAAAAGCAACTGCTTATATTTCGGG GCAAATTAGCAGATTAAATAGTGGTCTTAAAAC TCCATATGCTAATGGTTAGATGGTTATATTACA ATCATTTTATATTTTTTACATTATTAACATTCA CTTATAGATTC (SEQ ID No. 26) |
| SNP4 | A:T | 66488313 | 3' UTR | TCAATTTCCAAATGCATTGCAGTTGGCAAGGGT ATATGGTCCTAGAGTTACAAGTTCTACTGAAGC CACAGGAACACAGGGAAGCTGCATCTTTTTTTC TAGCACTTAATGATACCAGCACATTTATCTGAG CTTTGGGGGTACCAATTTTCA[A/T]ATTGAATTG AAAAATAATCATAAAGTGCCTAGAAATTCTTAA GTGCAACACTGTACATAAATGTTTTTGAAGTGA |

TABLE 7-continued

Details of polymorphisms identified in the MSTN flanking region.

| SNP ID | SNP | Location (bp) on ECA18 (EquCab2) | Structure | Flanking sequences |
|---|---|---|---|---|
| | | | | ACTCTCTTCTCTACTGCTTATCAGTTTAGTAAGT TAGCTATAAAGCAGTGACTAAGTCTATGAG (SEQ ID No. 27) |

Example 3

MSTN Ins227 bp Polymorphism (Chr18g.66495327Ins227 bp66495326)

This insertion polymorphism is located on Chromosome 18 of *Equus caballus* at position 66495327Ins227 bp66495326 reverse strand of the Horse Genome Sequence (*Equus caballus* Version 2.0) which can be viewed at www.broad.mit.edu/mammals/horse/.

The horse genome EquCab2 assembly is a Whole Genome Shotgun (WGS) assembly at 6.79× and was released in September 2007. A female Thoroughbred named "Twilight" was selected as the representative horse for genome sequencing. (Wade C. M., et al *Science* 326, 865-7).

The project coordination and genome sequencing and assembly is provided by the Broad Institute. The N50 size is the length such that 50% of the assembled genome lies in blocks of the N50 size or longer. The N50 size of the contigs is 112.38 kb, and the total length of all contigs is 2.43 Gb. When the gaps between contigs in scaffolds are included, the total span of the assembly is 2.68 Gb. The horse EquCab2 was annotated using a standard Ensembl mammalian pipeline. Predictions from vertebrate mammals as well as horse proteins have been given priority over predictions from non-vertebrate mammals. The set of predictions was been compared to 1:1 homologues genes in human and mouse, and missing homologs in the horse annotation have been recovered using exonerate. Horse and human cDNAs have been used to add UTRs to protein based predictions. The final gene-set comprises 20,737 protein-coding genes, 2,863 identified as pseudogenes and 1,580 classified as retro-transposed genes.

Further details of the Ins227 bp structural polymorphism are as follows:

Polymorphism: 66495327Ins227 bp66495326
EquCab2.0 SNP_ID: not detected in EquCab2.0 database. No report of insertion in on-line bioinformatics resources.

Genomic location of polymorphism: 5'UTR
Polymorphism type: Insertion
PCR Gel-Based Assay A PCR-based assay for allele size discrimination may be designed using the following primers:

MI_F    ATCAGCTCACCCTTGACTGTAAC (SEQ ID No. 17)

MI_R    TCATCTCTCTGGACATCGTACTG (SEQ ID No. 18)

Normal allele—Product Size 600 bp
Insertion227 bp allele—Product size 827 bp

Example 4

Polymorphisms in Linkage Disequilibrium with MSTN-66493737 SNP

3'UTR MSTN SNPs

Four SNPs in the 3'UTR of MSTN (SNPs 1 to 4—see Tables 6 and 7 above) are in linkage disequilibrium with MSTN 66493737 (T/C) and may be used as alternative predictive tests for racing performance, either alone or in combination with MSTN-66493737 and/or other polymorphisms.

Ins227 bp Polymorphism

Pairwise tests of linkage disequilibrium (LD) were performed between MSTN-g.66493737C/T and Ins227 bp.

The LD between MSTN-66493737 and Ins227 bp was $r^2=0.73$

In the example below, with one exception (Sample 12) the Ins227 bp polymorphism was in complete linkage disequilibrium with the C-allele at MSTN_66493737 (T/C). Sample 12 may represent the result of a recombination event (evidence from heterozygous state at SNP2).

TABLE 8

Linkage disequilibrium of 3'UTR SNPs, and MSTN-66493737(T/C)

| Sample ID | MSTN_66493737 (T/C). | SNP1 (Real) | SNP2 | SNP3 (Real) | SNP4 | Insertion |
|---|---|---|---|---|---|---|
| 7 | C:C | C:C | T:T | A:A | A:A | Insertion 227 bp/Insertion 227 bp |
| 8 | C:C | C:C | T:T | A:A | A:A | Insertion 227 bp/Insertion 227 bp |
| 9 | C:C | C:C | T:T | A:A | A:A | Insertion 227 bp/Insertion 227 bp |
| 11 | C:C | C:C | T:T | A:A | A:A | Insertion 227 bp/Insertion 227 bp |
| 12 | C:C | C:C | C:T | A:A | A:A | Insertion 227 bp/Normal |
| 3 | C:T | A:C | T:T | A:G | A:A | Insertion 227 bp/Normal |

TABLE 8-continued

Linkage disequilibrium of 3'UTR SNPs, and MSTN-66493737(T/C)

| Sample ID | MSTN_66493737 (T/C). | SNP1 (Real) | SNP2 | SNP3 (Real) | SNP4 | Insertion |
|---|---|---|---|---|---|---|
| 4 | C:T | A:C | T:T | A:G | A:A | Insertion 227 bp/Normal |
| 10 | C:T | A:C | T:T | A:G | A:A | Insertion 227 bp/Normal |
| 13 | C:T | A:C | T:T | A:G | A:A | Insertion 227 bp/Normal |
| 14 | C:T | A:C | T:T | A:G | A:A | Insertion 227 bp/Normal |
| 2 | T:T | A:A | T:T | G:G | A:A | Normal/Normal |
| 5 | T:T | A:A | T:T | G:G | A:A | Normal/Normal |
| 6 | T:T | A:A | T:T | G:G | A:A | Normal/Normal |
| 15 | T:T | A:A | T:T | G:G | A:A | Normal/Normal |
| 1 | T:T | A:C | T:T | A:G | A:T | Normal/Normal |

In 14 of the 15 sequenced samples, the Ins227 bp allele was in concordance with the C-allele at g.66493737C>T. As complete concordance was not observed, we genotyped a set of n=165 samples to determine the extent of concordance between the Ins227 bp and g.66493737C>T polymorphisms. We performed parallel association tests for the same set of samples to evaluate the relative performance of the two polymorphisms as predictors of optimum racing distance. The g.66493737C>T SNP performed better in an association test with best race distance (P=$5.24 \times 10^{-13}$) than the Ins227 bp polymorphism (P=$5.54 \times 10^{-10}$). Analysis of the sequence surrounding g.66493737C>T indicated that alternate alleles may result in the gain of a putative Homeobox C8/Hox-3alpha transcription factor binding site and/or the disruption of putative Distal-less homeobox 3, E2F and Pdx1 transcription factor binding sites.

Chromosome 18 SNPs

Figure 6:
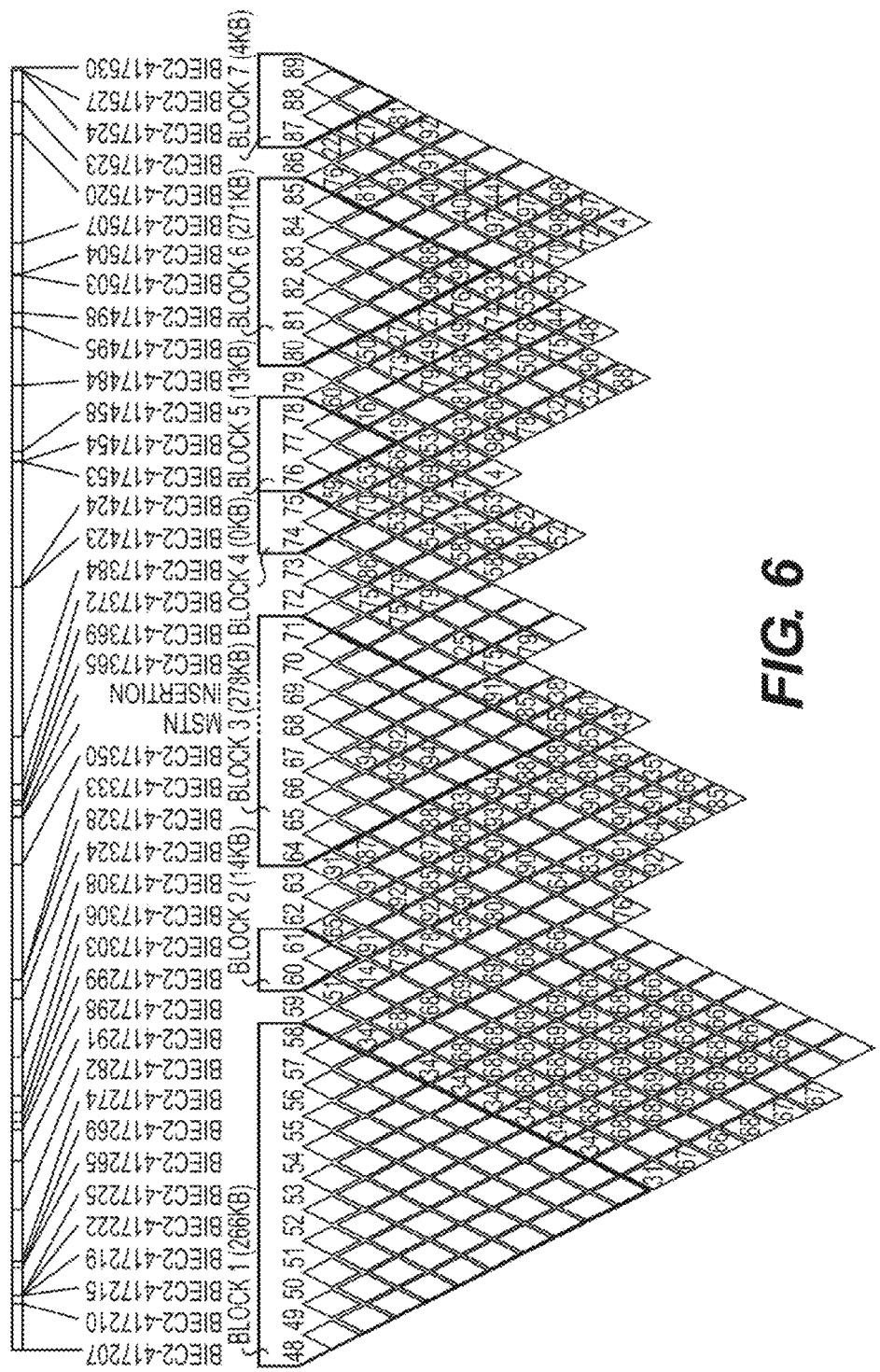
FIG. 6 is a visual representation of haplotype blocks across a 1.7 Mb region on chromosome 18. The g.66493737 C>T SNP was included in block 3, BIEC2-417495 was included in block 6.
Figure 7A:
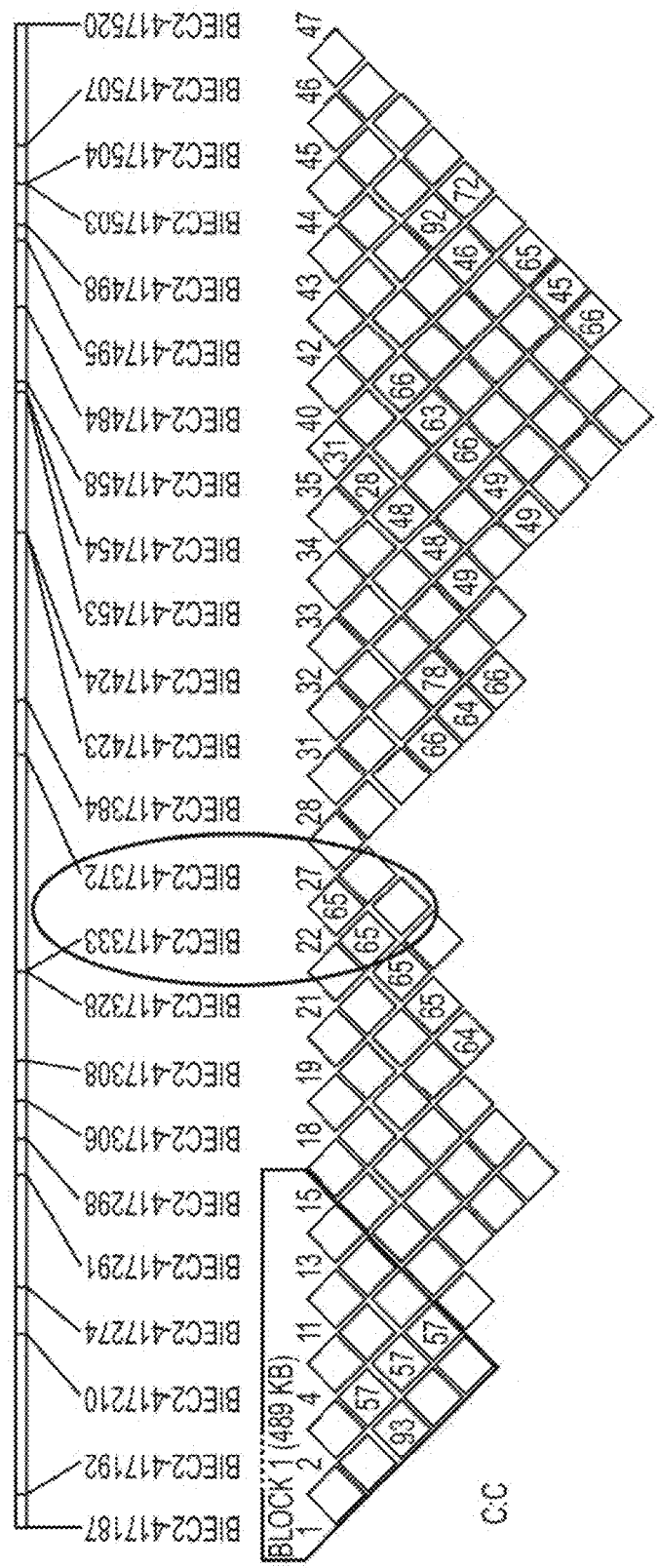
FIGS. 7A-C are visual representations of haplotype blocks across a 1.7 Mb region on chromosome 18 generated from samples that are C/C (to represent C-chromosomes), T/T (to represent T-chromosomes) and ALL (i.e. reconstructed from genotypes for C/C, C/T and T/T individuals). Recombinant events are shown in FIG. 7D.
Figure 7B:
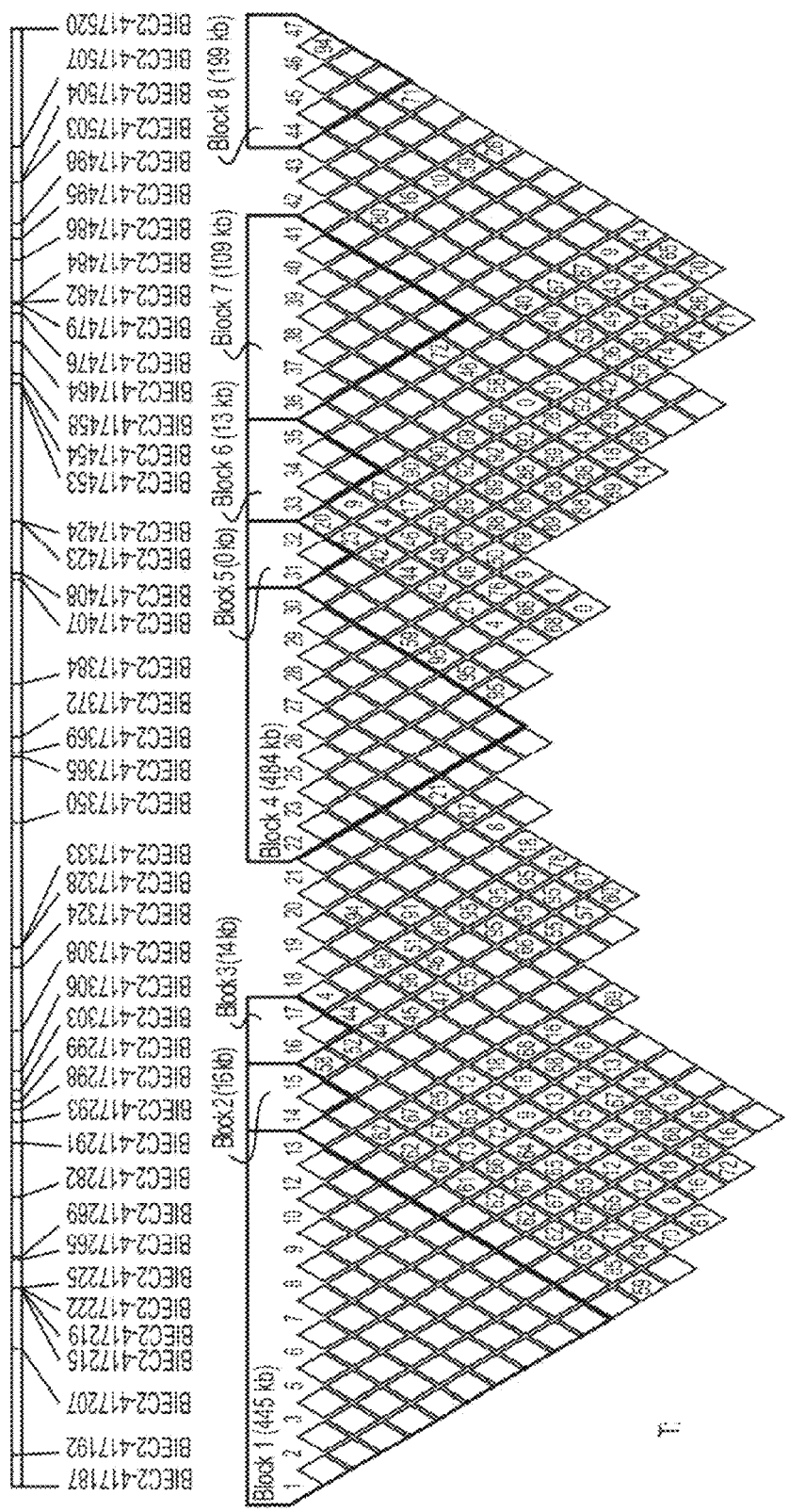
Figure 7C:
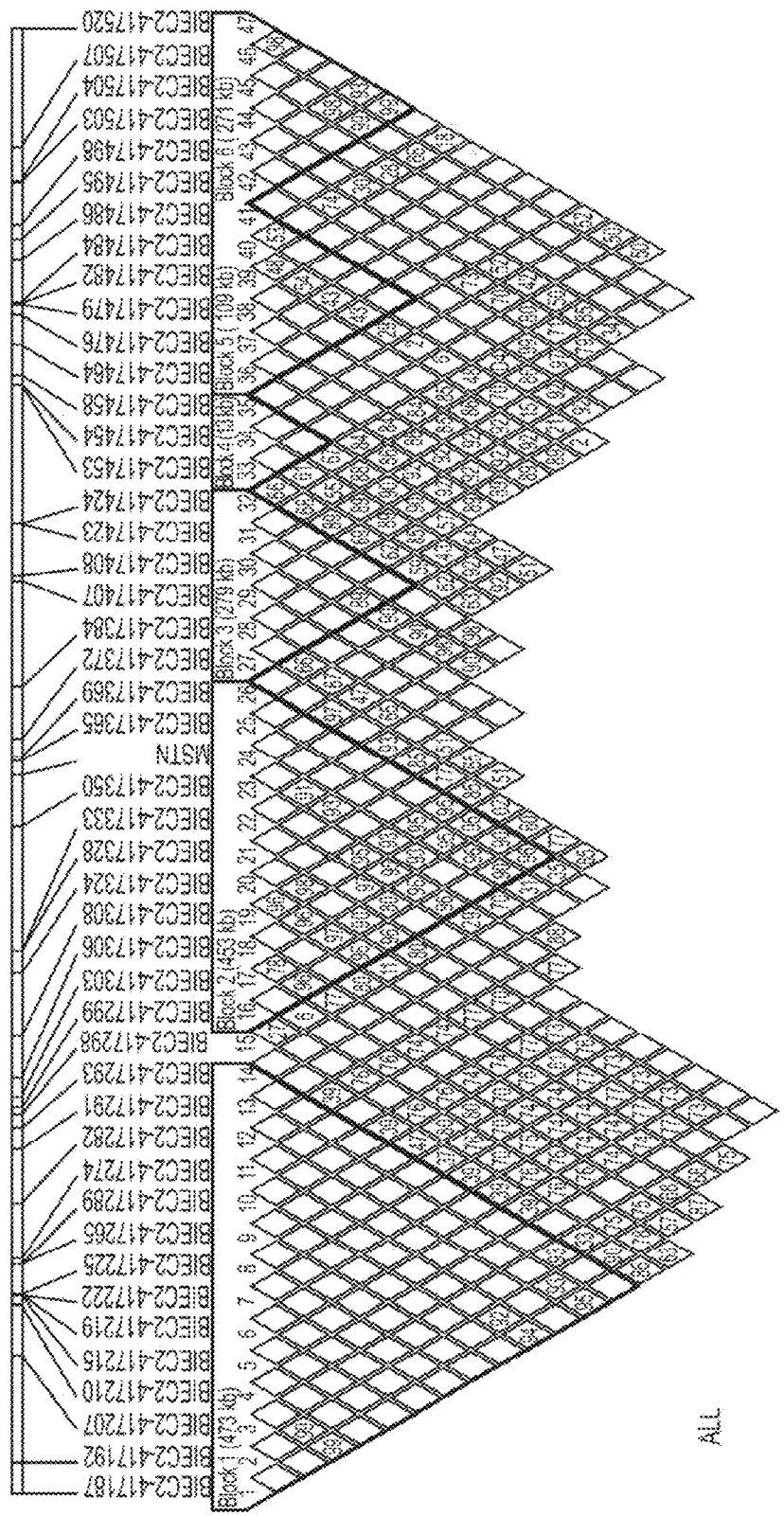
Figure 7D:
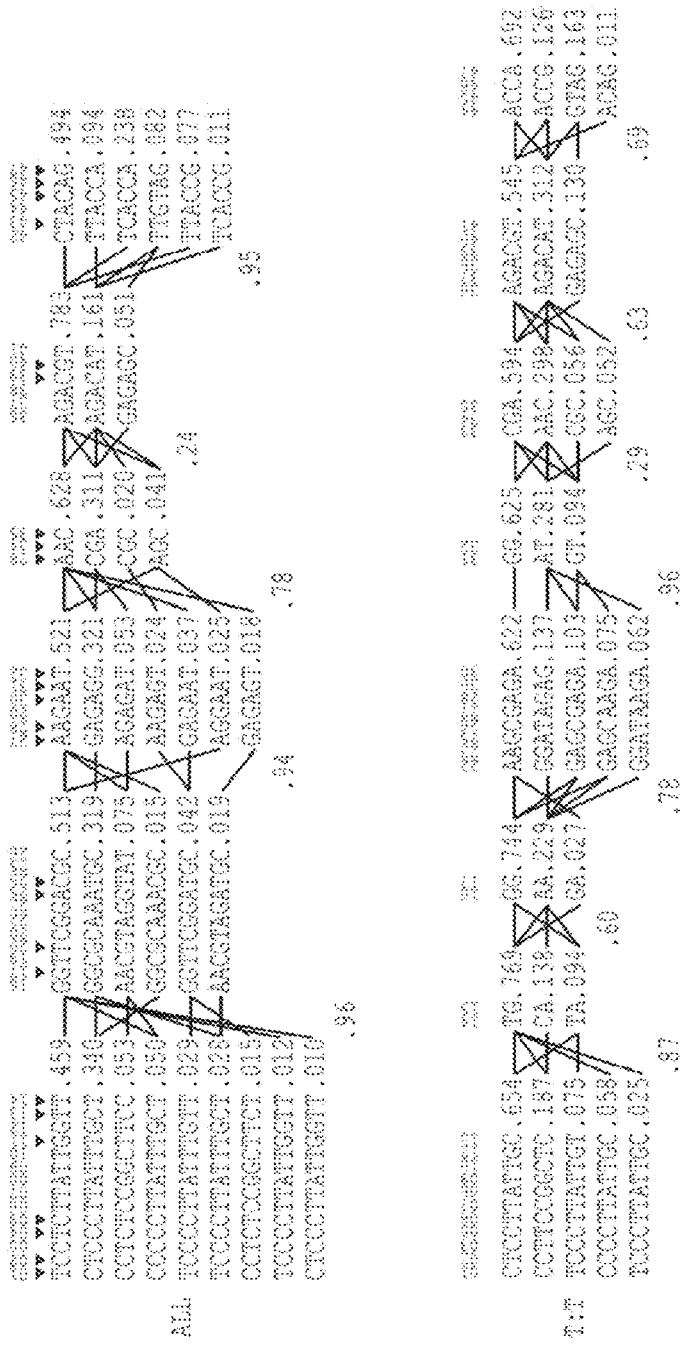

Pairwise tests of linkage disequilibrium (LD) were performed between g.66493737C>T and the 1,373 chromosome 18 SNPs represented on the genotyping array (Equine SNP50 genotyping BeadChips). LD was highest between g.66493737C>T and BIEC2-417495 ($r^2$=0.86). Seven discrete haplotype blocks were identified in the 1.7 Mb peak of association on chromosome 18. The g.66493737C>T SNP was included in block 3; BIEC2-417495 was included in block 6 (FIG. 6).

SUMMARY

We focused on comprehensively evaluating variation in the MSTN gene by re-sequencing ~2 kb of the 3' and 5' flanking sequences. Four novel 3' UTR SNPs and a 227 bp SINE insertion (Ins227 bp) polymorphism located 146 bp upstream of the coding region start site were identified (see Example 2 above). We investigated whether the 3' UTR SNPs may abrogate existing or create de novo putative miRNA binding sites, as has been described for MSTN influenced phenotypic variation in Texel sheep (Clop et al. 2006). However, there was no evidence for alterations in putative miRNA binding sites. Next, because of the close proximity to the transcriptional start site, we considered the Ins227 bp polymorphism as a strong functional candidate contributing to variation in racing performance. However, a comparative evaluation of association using the same set of samples (n=165) demonstrated that the g.66493737C>T SNP displayed a stronger association (P=$5.24 \times 10^{-13}$) with best race distance than the Ins227 bp polymorphism (P=$5.54 \times 10^{-10}$).

An evaluation of LD showed that the strongest association was between g.66493737C>T and the most significant SNP in the GWAS study, BIEC2-417495. A comparison of trait association in the same set of samples (n=118) confirmed the superior power of the g.66493737C>T SNP (P=$1.02 \times 10^{-10}$) in the prediction of best race distance when compared with BIEC2-417495 ($P_{unadj.}$=$1.61 \times 10^{-9}$). The significance values and genotype frequencies for the top SNPs in the GWAS and the g.66493737C>T SNP are shown in Table 9. In addition, we investigated whether g.66493737C>T may interact with other SNPs represented on the EquineSNP50 genotyping array; however, no significant interaction was observed to influence best race distance (P>0.0001 for all interactions). Therefore, the effect of genotype on racing phenotype is highly likely a result of the previously reported variation in the MSTN gene at locus g.66493737C>T.

TABLE 2

Significance values (unadjusted and Bonferroni corrected P values) for the top SNPs associated with optimum race distance.

| CHR | SNP | UNADJ P | BONF. P | A1 | A2 | A11 | A12 | A22 |
|---|---|---|---|---|---|---|---|---|
| 18 | g.66493737C > T | 1.02E−10 | N/A | T | C | 0.1538 | 0.5962 | 0.2500 |
| 18 | BIEC2-417495 | 1.61E−09 | 6.58E−05 | T | C | 0.1709 | 0.5983 | 0.2308 |
| 18 | BIEC2-417423 | 3.55E−08 | 0.001454 | G | A | 0.1017 | 0.5169 | 0.3814 |
| 18 | BIEC2-417372 | 6.21E−08 | 0.002545 | G | A | 0.0932 | 0.5424 | 0.3644 |
| 18 | BIEC2-417274 | 8.08E−08 | 0.003312 | T | G | 0.1864 | 0.6017 | 0.2119 |
| 18 | BIEC2-417210 | 3.13E−07 | 0.01281 | C | T | 0.2119 | 0.5763 | 0.2119 |
| 18 | BIEC2-417524 | 4.87E−07 | 0.01995 | G | A | 0.1186 | 0.5763 | 0.3051 |
| 18 | BIEC2-417507 | 5.09E−07 | 0.02086 | C | A | 0.1368 | 0.5897 | 0.2735 |

A11: genotype frequency for homozygotes (allele 1) in the population (n=118); A12: genotype frequency for heterozygotes; A22 genotype frequency for homozygotes (allele 2). Correction for multiple testing was not applied for g.66493737C>T; however, the association remains stronger ($P_{Bonf.}$=4.18×10$^{-6}$) after application of a correction factor.

It is important to note that the sample size used for the present study is relatively small. However, the results of the quantitative trait GWAS demonstrate that the sample size used was sufficient to detect a major genetic effect such as that manifested at the MSTN locus. A lower sample size requirement for GWAS in the Thoroughbred is supported by population genomics analyses of this population in comparison to other horse breeds. These demonstrate that the extent of LD in the Thoroughbred is significantly greater than that measured in other horse populations, being comparable to LD estimates in inbred dog breeds (Wade et al. 2009). The high LD in Thoroughbreds is a reflection of low effective population size, which enables detection of associations with smaller sample sizes.

Example 5

Haplotype Analysis in the Region of MSTN

Genotypes for a subset of n=182 (C/C n=102, T/T n=80) horses were extracted from data generated for a sample of n=368 Thoroughbred DNA samples genotyped using EquineSNP50 Genotyping BeadChips (Illumina, San Diego, Calif.). DNA was quantified using Quant-iT PicoGreen dsDNA kits (Invitrogen, Carlsbad, Calif.) according to the manufacturer's instructions and the DNA concentrations were adjusted to 20 ng/µl. The EquineSNP50 Genotyping BeadChip (Illumina, San Diego, Calif.) contains approximately 54,000 SNPs ascertained from the EquCab2 SNP database of the horse genome and has an average spacing of 43.2 kb between adjacent variants. Genotyping was performed by laboratories at AROS Applied Biotechnology, Denmark and GeneSeek, USA. The samples genotyped for the present study were a subset of samples genotyped in three separate batches (Batch 1, n=96; Batch 2, n=92; Batch 3, n=228). We included four pairs of duplicate samples between Batch 1 and Batch 2, two additional pairs of duplicate samples between Batch 2 and Batch 3 and two pairs of duplicate samples within Batch 3 for QC purposes and observed greater than 99.9% concordance in seven of the eight pairs. A parent offspring trio was also included to verify Mendelian transmission of SNPs. We successfully genotyped 53,922 loci. All samples had a genotyping rate>90%. We omitted SNPs which had a genotyping completion rate<90% were monomorphic or had minor allele frequencies (MAF)<5% in our samples. We omitted 18,109 SNPs leaving 35,813 SNPs in our working build of the data and the overall genotype completion rate was 99.9%.

SNPs spanning a 1.7 Mb region on ECA18 containing the MSTN gene were extracted from the data. Haploview was used to calculate pairwise measures of LD among the 47 SNPs and was employed to create a visual representation of the data. Using the default method, the region was divided into blocks of strong LD using a standard block definition (Gabriel et al., 2002) based on confidence intervals for strong LD and minor allele frequencies>0.05.

We re-constructed haplotypes in n=204 C-chromosomes and n=160 T-chromosomes in C/C and T/T Thoroughbreds only, for 46 SNPs (BIEC2-417187-BIEC2-417520) extracted from the Equine SNP50BeadChip and the MSTN g.66493737C/T variant. The 47 SNP-haplotypes (FIG. 7) spanned the 1.7 Mb region at the MSTN gene locus that contained a set of eight SNPs with genome-wide significance of association with best race distance in a previous GWAS (Hill et al 2010, the entire contents of which is included herein by reference). The C-allele was observed on a single haplotypic background spanning 273 kb (i.e. no variation was detected between BIEC2-417333-BIEC-417372), and only minimal variation was detected in a single proximal region (Block 1) located 439 kb upstream of the MSTN g.66493737C/T locus. This indicates haplotype conservation between the Ins227 bp and g.66493737C/T polymorphisms on g.66493737C-chromosomes. In contrast, the T-allele arises on a complex genetic background, with multiple haplotype blocks across the region, and considerable variation (FIG. 7) within the haplotype block (Block 4, spanning 484 kb) containing the MSTN g.66493737C/T SNP (see FIG. 7). These data are consistent with a single introduction of the C-allele at the foundation stages of the Thoroughbred.

Further haplotype analysis detected no background variation (MAF>0.05) on C-chromosomes (i.e. g.66493737C) between BIEC2-417333 and BIEC2-417372. i.e. an invariable 273096 kb haplotype block, containing both the Ins227 bp polymorphism and g.66493737C>T SNP.

Example 6

Assays for Predicting the Athletic Performance Potential of a Subject

The test for speed/stamina described in PCT/IE2009/000062, the entire contents of which is incorporated herein by reference, may be designed alternatively using an assay for any genetic variants in linkage disequilibrium with locus MSTN_66493737 (T/C). For example, the Ins227 bp polymorphism or BIEC2-417495. Alternatively, an assay for predicting the athletic performance potential of a subject may be based on a combination of more than one polymorphism.

Figure 2:
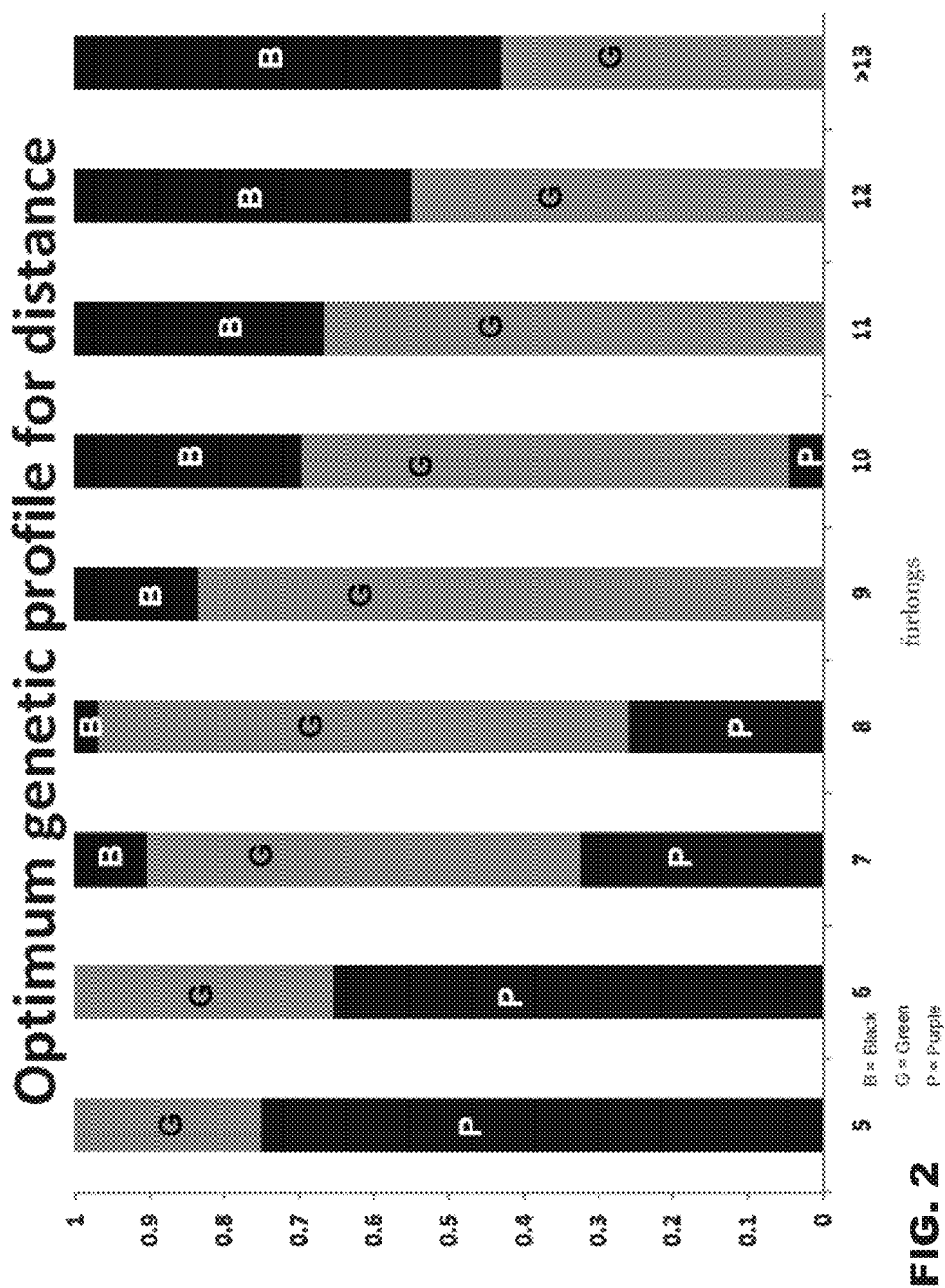
FIG. 2 is a bar chart showing the distribution of MSTN 66493737 (T/C) SNP genotypes in Thoroughbred subpopulations.

Validation of a test for association may be performed by genotyping 192 samples for validation of linkage between Ins227 bp and MSTN_66493737 (T/C) and association with retrospective racing performance traits (e.g. Best race distance). The Ins227 bp genotypes will similarly be predictive of best race distance and may correlate with predictions based on the MSTN_66493737(T/C) SNP. Examples of prediction of phenotypes are given in FIGS. 1 and 2.

The Ins227 bp polymorphism is located 1590 bp from the g.66493737C>T SNP.

The greater association between g.66493737C>T and best race distance than the Ins227 bp polymorphism does not preclude the Ins227 bp polymorphism being the functional variant. Functional studies will need to be performed to determine the functional variant.

Notwithstanding this, both/either of these polymorphisms may be used to predict best race distance.

Thoroughbred horses excel in both sprint (<1,500 m) and longer distance (>1,800 m) races. Horses competing in middle distance races ('milers' and 'middle distance') may be considered either 'sprinters' or 'stayers' and the way in which a race is executed by the rider often reflects the trainer's perceived sprinting and endurance ability of the horse. Within the industry horses may be described as sprinters based on their conformation and usually have a stockier and more muscular stature and are faster maturing. They usually race as 2 year olds and over shorter distances as 3 year olds. Individuals perceived to be longer distance animals may be referred to as 'backward' requiring more time to mature and running over longer distances as 3 year olds. In some regions (e.g. Australia) breeders attempt to breed only faster 'sprint' type horses. For example, in the USA Group 1 races>10 f are limited (9% USA, 23% Australia, 28% Britain,) and in Australia 37% of Group 1 races are competed over distances 5-7 f compared to 20% in USA and just 12% in Britain. These selection pressures favour C-alleles, which is reflected in the distribution of genotypes among a sample of elite mares and stallions sampled in Australia (n=43; C/C, 0.41; C/T, 0.47; T/T, 0.12).

In some aspects, the invention provides a simple DNA based method (genotype test) for predicting the elite sprint race performance of a thoroughbred race horse based on the presence or absence of a SNP or other structural DNA variant (e.g. insertion polymorphism) in one or more exercise response gene. For example the genotype test may be based on a SNP or insertion polymorphism in the MSTN gene and flanking sequences. Details of the SNPs and insertion polymorphism that may be used to predict the elite sprint race performance of a thoroughbred race horse are given in the appendices. It will be appreciated that the genotypic test may be based on a combination of any one or more of these polymorphisms.

Applications of the Assay

Considering the association between DNA variants such as Chr18g.66495327Ins227 bp66495326 and MSTN 66493737 (T/C) the test may be applied in practice in the following ways:

1. Young Stock (Foals and Yearlings)
Informed selection and sales decisions can be made to:
  identify sprinters
  identify middle-distance/potential Derby winners with speed
  identify individuals with enhanced stamina
2. Horses-in-Training
Operating costs can be reduced and racing strategy can be fine tuned by:
  identifying the most precocious two-year olds
  horses can be trained and raced for optimal racing distance
3. Broodmares
Breeding outcomes can be optimised by:
  focusing on optimal breeding mares
  selecting compatible stallions
4. Stallions
A stallions potential can be promoted by:
  predicting stamina index for young stallions (5 year advantage)
  attracting compatible mares to enhance stallion profile For example, for the Ins227 bp polymorphism for foals, young stock and horses-in-training selection of individuals may be made for individuals most likely to perform well as two year olds (Ins227 bp/Ins227 bp and Ins227 bp/Normal) and against 'backward' individuals (industry terminology for less physically developed young Thoroughbreds) that may benefit from waiting to race until they are three years old (Normal/Normal). Breeding objectives may be more confidently met by selecting Ins227 bp/Ins227 bp individuals for short distance racing, Ins227 bp/Normal individuals for middle-distance racing and Normal/Normal individuals for racing requiring greater stamina. For stallion owners, prediction of a stallion's genetic stamina index at the outset of a stud career (five years are required to estimate S.I. from retrospective three year old progeny racing performance) will immediately enhance a young stallion's profile and promote their genetic potential to mare owners. This in turn will enable mare owners, with targeted breeding strategies, to better select stallions to achieve specific breeding objectives. To eliminate uncertainty from a mating outcome (unless both sire and dam are homozygous) it will be necessary to genotype the foal, enabling selection of individuals for a targeted breeding outcome.

Example 7

Application of the Assay to Determine Speed Measured by GPS

We hypothesized that speed parameters measured using field technologies (GPS) in a cohort of horses-in-training may be influenced by g.66493737C>T genotypes at the myostatin locus.

Study Animals and Training Protocol

A subset of horses (n=85) from a group of Thoroughbred Flat racehorses (n=102) previously evaluated from a single training stable for physiological performance parameters during training (March-November) in 2007 and 2008 (Fonseca et al., 2010) were included in the current study. The horses included were chosen based on their training stage and fitness in order to make up the most homogeneous group. The study cohort comprised of 55 two-year-olds (18 males and 37 females) and 30 three-year-olds (11 males and 19 females). The criteria for inclusion in the study cohort were each horse must have completed at least 2 WDs prior to the GPS recording (i.e. GPS recordings were taken for ≥3 accWD) and had for which satisfactory GPS and HR recordings for work days (WD, an exercise workout which simulates a race) in the training period (March to November 2007 or March to November 2008); the GPS and HR data associated with the greatest number of accumulated WD (accWD) for each horse was used.

The training protocol for the horses has been described previously (Fonseca et al., 2010). Briefly, horses were trained six days per week on an outdoor all-weather gallop 1,500 m in length with a 2.7% incline for the final 800 m. The training program consisted of progressive stages gradually introducing 'fast' workouts (WD) as training progressed. WD generally consisted of gallop distances 800-1,000 m. Training was modified and adapted to each individual animal based on soundness, fitness and aptitude. Following the onset of WD, horses were entered into competitive races dependant on their perceived fitness and performance. All decisions on the training and racing schedule were made by a single trainer.

Experimental Protocol and Data Collection

Measured data were only recorded for horses undergoing a WD which has been previously described (Fonseca et al. 2010). Each jockey carried a hand-sized GPS unit (GPSports Systems SPI10). After data collection and at the end of each day the GPS data were downloaded to an equine-specific software programme (Race watch Software, GPSports Systems SPI10). The GPS unit recorded variables including speed, time and distance as well as the exact map of each horse's exercise. Prior to the onset of the study, the entire gallop had been pre-recorded using one of the GPS units as previously described (Fonseca et al. 2010).

Phenotypes

All speed measurements were recorded from a distance of 800 m from the finish line as the total distance exercised on a WD differed slightly for each horse. Speed indices evaluated were based on previous work by Fonseca et al. (2010) and included maximal velocity ($V_{max}$), duration at $V_{max}$ ($V_{maxt}$), distance (m) travelled during six seconds before $V_{max}$ ($V_{maxD6b}$), distance (m) travelled during six seconds after $V_{max}$ ($V_{maxD6a}$) and distance (m) travelled during six seconds before and after $V_{max}$ ($V_{maxD6}$).

DNA Extraction and MSTN Polymorphism Genotyping.

Genomic DNA was extracted from fresh whole blood using the Maxwell 16 automated DNA purification system (Promega, Wis., USA). Genotyping was carried out using Taqman chemistry on the StepOnePlus™ Real-Time PCR System (Applied Biosystems, CA, USA). The assay consisted of forward primer 5'-CCAGGACTATTTGATAGCA-GAGTCA (SEQ ID No. 28), reverse primer 3'GACACAA-CAGTTTCAAAATATTGTTCTCCTT (SEQ ID No. 29) and two allelic-specific fluorescent dye labeled probes (VIC-AATGCACCAAGTAATTT (SEQ ID No. 30); 6-FAM-ATG-CACCAAATAATTT) (SEQ ID No. 31).

Statistical Analyses

Tests of association were performed using the PLINK Version 1.05 software package (Purcell; Purcell et al. 2007). The linear regression model was used to evaluate quantitative trait association at MSTNg.66493737C>T with the phenotypes: $V_{max}$, $V_{maxt}$, $V_{maxD6b}$, $V_{maxD6a}$ and $V_{maxD6}$. The following were included as covariates in the analyses as they had all been found to contribute to variation in speed indices (Fonseca et al., 2010): Age, Sex, accWD, Jockey and Going.

Results

MSTN genotypes

MSTNg.66493737C>T genotypes were determined for all individuals in the study. There were 21 (24.7%) C/C, 44 (51.7%) C/T and 20 (23.5%) T/T individuals, representing a normal distribution of the genotypes previously observed among a large cohort of Flat racehorses (Hill et al., 2010, the entire contents of which is incorporated herein by reference).

MSTN Genotype Association with Speed Indices

MSTNg.66493737C>T genotypes were significantly associated with $V_{maxD6}$ (P=0.0040), $V_{maxt}$ (P=0.0249), $V_{max}$ (P=0.0265) and $V_{maxD6a}$=0.0317) (Table 10). For each speed index the C/C cohort out-performed the C/T and T/T cohorts (Table 11). The mean distance (m) travelled was 3.8 m and 1.2 m greater in the C/C (195.7 m; 98.2 m) than the T/T (191.9 m; 96.9) cohort during the 6 seconds before and after $V_{max}$ ($V_{maxD6}$) and during the 6 seconds after $V_{max}$($V_{maxD6}$). $V_{max}$ was 0.31 m/s faster in the C/C (16.6 m/s) cohort than the T/T (16.29 m/s) cohort and $V_{max}$ was maintained ($V_{maxt}$) for 2.05 s longer in the C/C (7.3 s) than the T/T (5.25 s) cohort.

TABLE 10

Association test results between measured speed variables and the MSTNg.66493737C > T SNP

| | TEST | NMISS | BETA | STAT | P |
|---|---|---|---|---|---|
| Acc6b | ADD | 78 | 0.0074 | 0.5426 | 0.5893 |
| | GENO_2DF | 78 | | 0.2990 | 0.8611 |
| Dist6 | ADD | 74 | −2.4790 | −3.1470 | 0.0026 |
| | GENO_2DF | 74 | | 11.0500 | 0.0040 |
| Dist6a | ADD | 78 | −0.7972 | −1.9090 | 0.0608 |
| | GENO_2DF | 78 | | 6.9040 | 0.0317 |
| Dist6b | ADD | 75 | 0.8968 | 0.1695 | 0.8660 |
| | GENO_2DF | 75 | | 1.3920 | 0.4985 |
| Tvmax | ADD | 81 | −1.0640 | −2.1040 | 0.0392 |
| | GENO_2DF | 81 | | 7.3850 | 0.0249 |
| Vmax | ADD | 85 | −0.1613 | −2.5260 | 0.0138 |
| | GENO_2DF | 85 | | 7.2620 | 0.0265 |

TABLE 11

Mean values for speed parameters for each genotype.

| GENO | T/T | T/C | C/C | CC:TT |
|---|---|---|---|---|
| Dist6 (m) MEAN | 191.9 | 194.7 | 195.7 | 3.8 |
| Dist6a (m) MEAN | 96.93 | 98.23 | 98.16 | 1.23 |
| TVmax (s) MEAN | 5.25 | 7.366 | 7.3 | 2.05 |
| Vmax (m/s) MEAN | 16.29 | 16.48 | 16.6 | 0.31 |

These data have demonstrated that genotypes at the MSTNg.66493737C>T locus have a significant influence in the determination of individual differences in speed Example 8

MSTN Gene Expression in Resting Skeletal Muscle Before and after Training

The MSTNg.66493737C>T SNP has been found to be significantly associated with Thoroughbred horse racing phenotypes and significant reductions in Thoroughbred skeletal muscle gene expression for three 17 bp transcripts 400-1,500 base pairs downstream of the MSTN gene following a period of training have been observed (McGivney et al 2010 BMC Genomics, the entire contents of which is incorporated herein by reference). Together these findings demonstrate that the identified MSTN genotypes may influence MSTN gene expression. To investigate this, MSTN mRNA expression was measured in biopsies from the middle gluteal muscle from 60 untrained yearling Thoroughbreds (C/C, n=15; C/T, n=28; T/T, n=17) using two independent real time qRT-PCR assays. MSTN gene expression was also evaluated in a subset (n=33) of these animals using muscle RNA samples collected after a ten-month period of training. A significant association was observed between genotype and mRNA abundance for the untrained horses (assay I, P=0.0237; assay II, P=0.003559), with the C/C cohort having the highest MSTN mRNA levels, the T/T group the lowest levels and the C/T group intermediate levels. Following training there was a significant decrease in MSTN mRNA (−3.35-fold; P=$6.9 \times 10^{-7}$) which was most apparent for the C/C cohort (−5.88-fold, P=0.001). These results show a significant association between phenotype, genotype and gene expression at the MSTN gene in Thoroughbred racehorses.

MSTN Gene Expression

MSTN mRNA expression in two independent real-time qRT-PCR assays (Table 12) has been investigated in resting skeletal muscle (gluteus medius) from biopsy samples that had been collected for n=60 untrained yearlings (C/C, n=15; C/T, n=28; T/T, n=17).

TABLE 12

Primer sequences for qRT-PCR assays for MSTN gene expression and TTN reference gene expression

| Primer Name | Target Gene | Location | Sequence | |
|---|---|---|---|---|
| TTN_FOR | Titin (TTN) | Exon 357 | gcatgacacaactggaaagc | (SEQ ID No. 32) |
| TTN_REV | Titin (TTN) | Exon 357 | aactttgccctcatcaatgc | (SEQ ID No. 33) |
| MSTN1-2_FOR | Myostatin (MSTN) | Exon 1 | tgacagcagtgatggctctt | (SEQ ID No. 34) |
| MSTN1-2_REV | Myostatin (MSTN) | Exon 2 | ttgggttttccttccacttg | (SEQ ID No. 35) |
| MSTN2-3_FOR | Myostatin (MSTN) | Exon 2 | ttcccaagaccaggagaaga | (SEQ ID No. 36) |
| MSTN2-3_REV | Myostatin (MSTN) | Exon 3 | cagcatcgagattctgtgga | (SEQ ID No. 37) |

We found a significant association with genotype for the MSTN 66493737 (T/C) SNP (P=0.003559). The C/C genotype cohort had higher MSTN mRNA levels (654.3±354.3; 613.7±327.0) than either of the C/T (405.7±234.1; 368.6±213.6) and T/T (350.1±185.5; 348.1±167.2) cohorts (FIG. 10).

It was also found that MSTN gene expression is significantly down-regulated (−4.2-fold, P=0.0043) following a period of training. In the Thoroughbred horse skeletal muscle transcriptome the greatest reduction in gene expression following a period of training is MSTN gene expression.

Results from analyses of gene expression generated since our initial report [Hill et al, 2010, the entire contents of which is incorporated herein by reference] of an association between MSTN genomic variation and optimum racing distance in Thoroughbreds support the hypothesis that the MSTN gene is functionally relevant to racing performance variation. In a transcriptome-wide investigation using digital gene expression (DGE) technology, we identified the greatest alteration in mRNA abundance in transcripts from MSTN in Thoroughbred skeletal muscle following a ten-month period of exercise training Seventy-four annotated transcripts were differentially expressed between pre- and post-training states and among the 58 genes with decreased expression, MSTN mRNA transcripts were the most significantly reduced (−4.2-fold, P=0.0043) (McGivney et al. 2010, the entire contents of which is incorporated herein by reference).

Example 9

The mechanism by which the g.66493737C>T sequence variant may affect the muscle phenotype in horses is not clear; however we propose a direct effect of the SNP on the control of myocyte development. Myostatin is a growth and differentiation factor (GDF8) that functions as a negative regulator of skeletal muscle mass development and results in hypertrophied muscle phenotypes in a range of mammalian species, including horse. Consistent with this role myostatin has been shown to repress the proliferation and differentiation of cultured myocytes (Thomas et al. 2000; Langley et al. 2002; Joulia et al. 2003). The proliferation of myoblasts is determined by the control and progression of the cell cycle, a role which has been assigned to members of the E2F family of transcription factors (Polager & Ginsberg 2009). The g.66493737C>T SNP is located within the sequence of a putative E2F transcription factor binding site in intron 1 of the MSTN gene. It may therefore be plausible to propose a mechanism by which allele-specific binding of E2F to myostatin influences the growth and development of myocytes following signalling from upstream effector proteins such as retinoblastoma protein (Hallstrom & Nevins 2009). Genotype-specific gene expression studies will shed light on the allele-specific effect on function.

The predictive tests described herein may be applied to select individuals with high or low genetic potential for racing success. These tests can be performed on an individual at any stage in the life cycle e.g. Day 1 (birth), prior to sales (i.e. yearlings, 2 year olds etc), during racing career (i.e. from 2 years old), during breeding (i.e. up to approx 25 years). Also, the tests may be applied to select appropriate stallion—mare matches for mating based on the genetic make-up of mare and stallion.

Modifications and additions can be made to the embodiments of the invention described herein without departing from the scope of the invention. For example, while the embodiments described herein refer to particular features, the invention includes embodiments having different combinations of features. The invention also includes embodiments that do not include all of the specific features described.

The invention is not limited to the embodiments hereinbefore described, which may be varied in construction and detail.

REFERENCES

Ballard J. W. & Dean M. D. (2001) The mitochondrial genome: mutation, selection and recombination. *Curr Opin Genet Dev* 11, 667-72.

Barrett J. C., Fry B., Maller J. & Daly M. J. (2005) Haploview: analysis and visualization of LD and haplotype maps. *Bioinformatics* 21, 263-5.

Barrett J. C. (2009) Haploview: Visualization and analysis of SNP genotype data. *Cold Spring Harb Protoc* 2009, pdb ip71.

Barrey E., Valette J. P., Jouglin M., Blouin C. & Langlois B. (1999) Heritability of percentage of fast myosin heavy chains in skeletal muscles and relationship with performance. *Equine Vet J Suppl* 30, 289-92.

Blier P. U., Dufresne F. & Burton R. S. (2001) Natural selection and the evolution of mtDNA-encoded peptides: evidence for intergenomic co-adaptation. *Trends Genet* 17, 400-6.

Bray M S, Hagberg J M, Pérusse L, Rankinen T, Roth S M, Wolfarth B, Bouchard C. The human gene map for performance and health-related fitness phenotypes: the 2006-2007 update. Med Sci Sports Exerc. 2009 January; 41(1): 35-73.

Buitrago M., Lorenz K., Maass A. H., Oberdorf-Maass S., Keller U., Schmitteckert E. M., Ivashchenko Y., Lohse M.

J. & Engelhardt S. (2005) The transcriptional repressor Nab1 is a specific regulator of pathological cardiac hypertrophy. *Nat Med* 11, 837-44.

Cartharius K., Frech K., Grote K., Klocke B., Haltmeier M., Klingenhoff A., Frisch M., Bayerlein M. & Werner T. (2005) MatInspector and beyond: promoter analysis based on transcription factor binding sites. *Bioinformatics* 21, 2933-42.

Clop A., Marcq F., Takeda H., Pirottin D., Tordoir X., Bibe B., Bouix J., Caiment F., Elsen J. M., Eychenne F., Larzul C., Laville E., Meish F., Milenkovic D., Tobin J., Charlier C. & Georges M. (2006) A mutation creating a potential illegitimate microRNA target site in the myostatin gene affects muscularity in sheep. *Nat Genet* 38, 813-8.

Cunningham E P, Dooley J J, Splan R K, Bradley D G. Microsatellite diversity, pedigree relatedness and the contributions of founder lineages to Thoroughbred horses. Anim Genet. 2001 December; 32(6):360-4.

Das J. (2006) The role of mitochondrial respiration in physiological and evolutionary adaptation. *Bioessays* 28, 890-901.

Dempsey and Wagner 1999 Exercise-induced arterial hypoxemia. J Appl Physiol. 1999 December; 87(6):1997-2006. Review. PMID: 10601141

Fukuda R, Zhang H, Kim J W, Shimoda L, Dang C V, Semenza GL.HIF-1 regulates cytochrome oxidase subunits to optimize efficiency of respiration in hypoxic cells. Cell. 2007 Apr. 6; 129(1):111-22.

Gordon D, Abajian C, Green P. Consed: a graphical tool for sequence finishing. Genome Res. 1998 March; 8(3):195-202.

Gramkow and Evans 2006 Gramkow H L, Evans D L. Correlation of race earnings with velocity at maximal heart rate during a field exercise test in Thoroughbred racehorses. Equine Vet J Suppl. 2006 August; (36):118-22. PMID: 17402405.

Grobet L., Martin L. J., Poncelet D., Pirottin D., Brouwers B., Riquet J., Schoeberlein A., Dunner S., Menissier F., Massabanda J., Fries R., Hanset R. & Georges M. (1997) A deletion in the bovine myostatin gene causes the double-muscled phenotype in cattle. *Nat Genet* 17, 71-4.

Gu J, Orr N, Park S D, Katz L M, Sulimova G, MacHugh D E, Hill E W. A genome scan for positive selection in thoroughbred horses. PLoS One. 2009 Jun. 2; 4(6):e5767.

Gunn H M. Muscle, bone and fat proportions and muscle distribution of thoroughbreds and quarter horses. In: Gillespie J R, Robinson N E eds. Equine exercise physiology 2. Davis, C A: ICEEP; 1987:253-264.

Gunn H. M. (1987) Muscle, bone and fat proportions and muscle distribution of thoroughbreds and quarter horses. In: *Equine exercise physiology 2: Proceedings of the Second International Conference on Equine Exercise Physiology*; San Diego, Calif. Aug. 7-11, 1986 (eds. By Gillespie J R & Robinson N E), pp. xiii, 810p. ICEEP Publications, Davis, Calif.

Harkins et al., 1993 Harkins J D, Hackett R P, Ducharme N G. Effect of furosemide on physiologic variables in exercising horses. Am J Vet Res. 1993 December; 54(12):2104-9. PMID: 8116946

Hallstrom T. C. & Nevins J. R. (2009) Balancing the decision of cell proliferation and cell fate. *Cell Cycle* 8, 532-5.

Hill E. W., McGivney B. A., Gu J., Whiston R. & Machugh D. E. (2010) A genome-wide SNP-association study confirms a sequence variant (g.66493737C>T) in the equine myostatin (MSTN) gene as the most powerful predictor of optimum racing distance for Thoroughbred racehorses. *BMC Genomics* 11, 552.

Hoppeler and Vogt, 2001 Muscle tissue adaptations to hypoxia. J Exp Biol. 2001 September; 204(Pt 18):3133-9. Review. PMID: 11581327

Jorgensen T. J., Ruczinski I., Kessing B., Smith M. W., Shugart Y. Y. & Alberg A. J. (2009) Hypothesis-driven candidate gene association studies: practical design and analytical considerations. *Am J Epidemiol* 170, 986-93.

Joulia D., Bernardi H., Garandel V., Rabenoelina F., Vernus B. & Cabello G. (2003) Mechanisms involved in the inhibition of myoblast proliferation and differentiation by myostatin. *Exp Cell Res* 286, 263-75.

Langley B., Thomas M., Bishop A., Sharma M., Gilmour S. & Kambadur R. (2002) Myostatin inhibits myoblast differentiation by down-regulating MyoD expression. *J Biol Chem* 277, 49831-40.

Love S, Wyse C A, Stirk A J, Stear M J, Calver P, Voute L C, Mellor D J. Prevalence, heritability and significance of musculoskeletal conformational traits in Thoroughbred yearlings. Equine Vet J. 2006 November; 38(7):597-603. PMID: 17228572

Martin Flück 2006 Functional, structural and molecular plasticity of mammalian skeletal muscle in response to exercise stimuli. The Journal of Experimental Biology 209, 2239-2248

Matoba S, Kang J G, Patino W D, Wragg A, Boehm M, Gavrilova O, Hurley P J, Bunz F, Hwang P M. p53 regulates mitochondrial respiration. Science. 2006 Jun. 16; 312 (5780):1650-3. Epub 2006 May 25.

McGivney B. A., Eivers S. S., MacHugh D. E., MacLeod J. N., O'Gorman G. M., Park S. D., Katz L. M. & Hill E. W. (2009) Transcriptional adaptations following exercise in thoroughbred horse skeletal muscle highlights molecular mechanisms that lead to muscle hypertrophy. *BMC Genomics* 10, 638.

McGivney B. A., McGettigan P. A., Browne J. A., Evans A. C., Fonseca R. G., Loftus B. J., Lohan A., MacHugh D. E., Murphy B. A., Katz L. M. & Hill E. W. (2010) Characterization of the equine skeletal muscle transcriptome identifies novel functional responses to exercise training. *BMC Genomics* 11, 398.

McPherron A. C., Lawler A. M. & Lee S. J. (1997) Regulation of skeletal muscle mass in mice by a new TGF-beta superfamily member. *Nature* 387, 83-90.

McPherron A. C. & Lee S. J. (1997) Double muscling in cattle due to mutations in the myostatin gene. *Proc Natl Acad Sci USA* 94, 12457-61.

Meiklejohn C. D., Montooth K. L. & Rand D. M. (2007) Positive and negative selection on the mitochondrial genome. *Trends Genet* 23, 259-63.

Mosher D S, Quignon P, Bustamante C D, Sutter N B, Mellersh C S, Parker H G, Ostrander E A. A mutation in the myostatin gene increases muscle mass and enhances racing performance in heterozygote dogs. PLoS Genet. 2007 May 25; 3(5):e79. Epub 2007 Apr. 30.

Polager S. & Ginsberg D. (2009) p53 and E2f: partners in life and death. *Nat Rev Cancer* 9, 738-48.

Purcell S. PLINK version 1.05. URL http://pngu.mgh.harvard.edu/purcell/plink/.

Purcell S., Neale B., Todd-Brown K., Thomas L., Ferreira M. A., Bender D., Maller J., Sklar P., de Bakker P. I., Daly M. J. & Sham P. C. (2007) PLINK: a tool set for whole-genome association and population-based linkage analyses. *Am J Hum Genet* 81, 559-75.

Revington M. Haematology of the racing Thoroughbred in Australia 2: haematological values compared to performance. Equine Vet J. 1983 April; 15(2):145-8. PMID: 6873047

Rivero J L, Ruz A, Marti-Korff S, Estepa J C, Aguilera-Tejero E, Werkman J, Sobotta M, Lindner A. Effects of intensity and duration of exercise on muscular responses to training of Thoroughbred racehorses. J Appl Physiol. 2007 May; 102(5):1871-82. Epub 2007 Jan. 25. PMID: 17255370.

Rivero J.-L., L, & Piercy R. J. (2008) Muscle physiology: responses to exercise and training. In: *Equine exercise physiology: the science of exercise in the athletic horse* (eds. by Hinchcliff K W, Kaneps A J & Geor R J), pp. ix, 463 p. Elsevier Saunders, Edinburgh.

Rivero J. L., Serrano A. L., Henckel P. & Aguera E. (1993) Muscle fiber type composition and fiber size in successfully and unsuccessfully endurance-raced horses. *J Appl Physiol* 75, 1758-66.

Rozen S. & Skaletsky H. (2000) Primer3 on the WWW for general users and for biologist programmers. *Methods Mol Biol* 132, 365-86.

Saleem A, Adhihetty P J, Hood D A. Role of p53 in mitochondrial biogenesis and apoptosis in skeletal muscle. Physiol Genomics. 2009 Mar. 3; 37(1):58-66. Epub 2008 Dec. 23. Links Sambrook, J. and D. Russell (2001). Molecular Cloning; A Laboratory Manual, Cold Spring Harbor Laboratory.

Schuelke M., Wagner K. R., Stolz L. E., Hubner C., Riebel T., Komen W., Braun T., Tobin J. F. & Lee S. J. (2004) Myostatin mutation associated with gross muscle hypertrophy in a child. *N Engl J Med* 350, 2682-8.

Seaman J, Erickson B K, Kubo K, Hiraga A, Kai M, Yamaya Y, Wagner P D. Exercise induced ventilation/perfusion inequality in the horse. Equine Vet J. 1995 March; 27(2): 104-9. PMID: 7607141

Suzanne S. Eivers, Beatrice A. McGivney, Rita G. Fonseca, David E. MacHugh, Katie Menson, Stephen D. Park, Jose-Luis L. Rivero, Cormac T. Taylor, Lisa M. Katz and Emmeline W. Hill* Exercise-induced skeletal muscle gene expression in unconditioned and conditioned Thoroughbred horses and associations with physiological variables. *Physiological Genomics*, In Preparation (2009)

Taylor C T, Colgan S P. Therapeutic targets for hypoxia-elicited pathways. Pharm Res. 1999 October; 16(10): 1498-505. Review. PMID: 10554089.

Tabor H. K., Risch N. J. & Myers R. M. (2002) Opinion: Candidate-gene approaches for studying complex genetic traits: practical considerations. *Nat Rev Genet* 3, 391-7.

Thiel G., Kaufmann K., Magin A., Lietz M., Bach K. & Cramer M. (2000) The human transcriptional repressor protein NAB1: expression and biological activity. *Biochim Biophys Acta* 1493, 289-301.

Thomas M., Langley B., Berry C., Sharma M., Kirk S., Bass J. & Kambadur R. (2000) Myostatin, a negative regulator of muscle growth, functions by inhibiting myoblast proliferation. *J Biol Chem* 275, 40235-43.

van Baren M. J. & Heutink P. (2004) The PCR suite. *Bioinformatics* 20, 591-3.

van Deursen et al. 1993 Skeletal muslces of mice deficient in muscle creatine kinase lack burst activity Cell 74: 621-631.

Wade C. M., Giulotto E., Sigurdsson S., Zoli M., Gnerre S., Imsland F., Lear T. L., Adelson D. L., Bailey E., Bellone R. R., Blocker H., Distl O., Edgar R. C., Garber M., Leeb T., Mauceli E., MacLeod J. N., Penedo M. C., Raison J. M., Sharpe T., Vogel J., Andersson L., Antczak D. F., Biagi T., Binns M. M., Chowdhary B. P., Coleman S. J., Della Valle G., Fryc S., Guerin G., Hasegawa T., Hill E. W., Jurka J., Kiialainen A., Lindgren G., Liu J., Magnani E., Mickelson J. R., Murray J., Nergadze S. G., Onofrio R., Pedroni S., Piras M. F., Raudsepp T., Rocchi M., Roed K. H., Ryder O. A., Searle S., Skow L., Swinburne J. E., Syvanen A. C., Tozaki T., Valberg S. J., Vaudin M., White J. R., Zody M. C., Lander E. S. & Lindblad-Toh K. (2009) Genome sequence, comparative analysis, and population genetics of the domestic horse. *Science* 326, 865-7.

Weatherby and Sons (1791) *An Introduction to a General Stud Book*. Weatherby and Sons, London.

Weber K, Bruck P, Mikes Z, Küpper J H, Klingenspor M, Wiesner R J. Glucocorticoid hormone stimulates mitochondrial biogenesis specifically in skeletal muscle. Endocrinology. 2002 January; 143(1):177-84.

Willett P. (1981) *The classic racehorse*. Stanley Paul, London.

Williamson S. A. & Beilharz R. G. (1998) The inheritance of speed, stamina and other racing performance characters in the Australian Thoroughbred. *J Anim Breed Genet* 115, 1-16.

Yang Q, Khoury M J, Botto L, Friedman J M, Flanders W D. Improving the prediction of complex diseases by testing for multiple disease-susceptibility genes. Am J Hum Genet. 2003 March; 72(3):636-49. Epub 2003 Feb. 14.

Young L E, Rogers K, Wood J L. Left ventricular size and systolic function in Thoroughbred racehorses and their relationships to race performance. J Appl Physiol. 2005 October; 99(4):1278-85. Epub 2005 May 26. PMID: 15920096

Zhou M., Wang Q., Sun J., Li X., Xu L., Yang H., Shi H., Ning S., Chen L., Li Y., He T. & Zheng Y. (2009) In silico detection and characteristics of novel microRNA genes in the *Equus caballus* genome using an integrated ab initio and comparative genomic approach. *Genomics* 94, 125-31.

The invention claimed is:

1. A method of training a Thoroughbred race horse for optimal racing distance, the method comprising the steps of:
   a) identifying a Thoroughbred race horse that is or may become sufficiently developed for race training,
   b) obtaining a biological sample from the horse,
   c) obtaining a genotypic analysis of a Chr18g.66495327Ins227 bp66495326 polymorphism in the biological sample from the horse; and
   d) training the horse based on results of the test,
   wherein:
      i) a horse with a Ins227 bp/Ins227 bp genotype in the Chr18g.66495327Ins227 bp66495326 polymorphism is trained to race as a sprinter,
      ii) a horse with a Ins227 bp/normal genotype in the Chr18g.66495327Ins227 bp66495326 polymorphism is trained to race over middle distances, or
      iii) a horse with a normal/normal genotype in the Chr18g.66495327Ins227 bp66495326 polymorphism is trained to race as a stayer.

2. The method of claim 1, wherein the horse has a Ins227 bp/Ins227 bp genotype in the Chr18g.66495327Ins227 bp66495326 polymorphism and is trained to race as a sprinter.

3. The method of claim 1, wherein the horse has a Ins227 bp/normal genotype in the Chr18g.66495327Ins227 bp66495326 polymorphism and is trained to race over middle distances.

4. The method of claim 1, wherein the horse has a normal/normal genotype in the Chr18g.66495327Ins227 bp66495326 polymorphism and is trained to race as a stayer.

5. The method of claim 1, wherein the horse is a two-year old.

6. The method of claim 2, wherein the horse is a two-year old.

7. The method of claim 4, wherein the horse is a three-year old.

8. The method of claim 1, further comprising obtaining a genotypic analysis of the MSTN-66493737 (T/C) SNP in the biological sample.

9. A method of breeding a Thoroughbred race horse with elite athletic performance potential, comprising the steps of:
   a) obtaining the result of a genotypic analysis of a Chr18g.66495327Ins227 bp66495326 polymorphism in a biological sample from a Thoroughbred broodmare;
   b) obtaining the result of a genotypic analysis of a Chr18g.66495327Ins227 bp66495326 polymorphism in a biological sample from a Thoroughbred stallion; and
   c) mating the broodmare with the stallion to produce a Thoroughbred offspring;
   wherein:
      i) the broodmare and the stallion each have a homozygous Ins227 bp/Ins227 bp genotype in the Chr18g.66495327Ins227 bp66495326 polymorphism, and the offspring has elite sprinting performance potential,
      ii) the broodmare and the stallion each have a homozygous normal/normal genotype in the Chr18g.66495327Ins227 bp66495326 polymorphism, and the offspring has stamina performance potential,
      iii) one of the broodmare or stallion has a homozygous normal/normal genotype in the Chr18g.66495327Ins227 bp66495326 polymorphism, and the other horse in the mating pair has a homozygous Ins227 bp/Ins227 bp genotype in the Chr18g.66495327Ins227 bp66495326 polymorphism, and the offspring has middle distance racing performance potential,
      iv) one of the broodmare or stallion has a homozygous Ins227 bp/Ins227 bp genotype in the Chr18g.66495327Ins227 bp66495326 polymorphism, and the other horse in the mating pair has a heterozygous Ins227 bp/normal genotype in the Chr18g.66495327Ins227 bp66495326 polymorphism, and the offspring has either elite sprinting performance potential or middle distance racing performance potential,
      v) one of the broodmare or stallion has a homozygous normal/normal genotype in the Chr18g.66495327Ins227 bp66495326 polymorphism, and the other horse in the mating pair has a heterozygous Ins227 bp/normal genotype in the Chr18g.66495327Ins227 bp66495326 polymorphism, and the offspring has either middle distance racing performance potential or stamina performance potential, or
      vi) the broodmare and the stallion each have a heterozygous Ins227 bp/normal genotype in the Chr18g.66495327Ins227 bp66495326 polymorphism, and the offspring has elite sprinting performance potential, middle distance racing performance potential, or stamina performance potential.

10. The method of claim 9, wherein the broodmare and the stallion each have a homozygous Ins227 bp/Ins227 bp genotype in the Chr 18g.66495327Ins227 bp66495326 polymorphism, and the offspring has elite sprinting performance potential.

11. The method of claim 9, wherein the broodmare and the stallion each have a homozygous normal/normal genotype in the Chr18g.66495327Ins227 bp66495326 polymorphism, and the offspring has stamina performance potential.

12. The method of claim 9, wherein one of the broodmare or stallion has a homozygous normal/normal genotype in the Chr18g.66495327Ins227 bp66495326 polymorphism, and the other horse in the mating pair has a homozygous Ins227 bp/Ins227 bp genotype in the Chr 18g.66495327Ins227 bp66495326 polymorphism, and the offspring has middle distance racing performance potential.

13. The method of claim 9, wherein one of the broodmare or stallion has a homozygous Ins227 bp/Ins227 bp genotype in the Chr 18g.66495327Ins227 bp66495326 polymorphism, and other horse in the mating pair has a heterozygous Ins227 bp/normal genotype in the Chr18g.66495327Ins227 bp66495326 polymorphism, and the offspring has either elite sprinting performance potential or middle distance racing performance potential.

14. The method of claim 9, wherein one of the broodmare or stallion has a homozygous normal/normal genotype in the Chr18g.66495327Ins227 bp66495326 polymorphism, and the other horse in the mating pair has a heterozygous Ins227 bp/normal genotype in the Chr18g.66495327Ins227 bp66495326 polymorphism, and the offspring has either middle distance racing performance potential or stamina performance potential.

15. The method of claim 9, wherein the broodmare and the stallion each have a heterozygous Ins227 bp/normal genotype in the Chr18g.66495327Ins227 bp66495326 polymorphism, and the offspring has elite sprinting performance potential, middle distance racing performance potential, or stamina performance potential.

16. The method of claim 9, further comprising the step of obtaining the genotype of the Chr18g.66495327Ins227 bp66495326 polymorphism in a biological sample from a foal produced by the mating.

17. The method of claim 9, further comprising the step of obtaining a genotypic analysis of the MSTN-66493737 (T/C) SNP in one or both of the biological sample from the Thoroughbred broodmare and the biological sample from the Thoroughbred stallion.

18. The method of claim 9, further comprising the step of obtaining the genotype of a MSTN-66493737 (T/C) SNP in a biological sample from a foal produced by the mating.

* * * * *

UNITED STATES PATENT AND TRADEMARK OFFICE
CERTIFICATE OF CORRECTION

PATENT NO. : 9,249,470 B2
APPLICATION NO. : 14/175696
DATED : February 2, 2016
INVENTOR(S) : Emmeline Hill et al.

It is certified that error appears in the above-identified patent and that said Letters Patent is hereby corrected as shown below:

IN THE SPECIFICATION

Col. 2, Line 32, "Ins227 bp" should read as --Ins227bp--.

Col. 3, Line 1, "Ins227 bp" should read as --Ins227bp--.

Col. 3, Line 29, "Ins227 bp" should read as --Ins227bp--.

Col. 4, Line 10, "Ins227 bp" should read as --Ins227bp--.

Col. 4, Line 39-40, "Chr18g.66495327Ins227 bp66495326" should read as --Chr18g.66495327Ins227bp66495326--.

Col. 4, Line 40, "Ins227 bp" should read as --Ins227bp--.

Col. 4, Line 42, "Ins227 bp/Ins 227 bp" should read as --Ins227bp/Ins227bp--.

Col. 4, Line 64-65, "Chr18g.66495327Ins227 bp66495326" should read as --Chr18g.66495327Ins227bp66495326--.

Col. 4, Line 65, "Ins227 bp" should read as --Ins227bp--.

Col. 4, Line 67, "Ins227 bp/Ins 227 bp" should read as --Ins227bp/Ins227bp--.

Col. 5, Line 14-15, "Chr18g.66495327Ins227 bp66495326" should read as --Chr18g.66495327Ins227bp66495326--.

Col. 5, Line 15, "Ins227 bp" should read as --Ins227bp--.

Signed and Sealed this
Twenty-first Day of June, 2016

Michelle K. Lee
*Director of the United States Patent and Trademark Office*

CERTIFICATE OF CORRECTION (continued)
U.S. Pat. No. 9,249,470 B2

Col. 5, Line 17, "Ins227 bp/Ins 227 bp" should read as --Ins227bp/Ins227bp--.

Col. 5, Line 24-25, "Chr18g.66495327Ins227 bp66495326" should read as --Chr18g.66495327Ins227bp66495326--.

Col. 5, Line 27, "Ins227 bp" should read as --Ins227bp--.

Col. 5, Line 28, "Chr18g.66495327Ins227 bp66495326" should read as --Chr18g.66495327Ins227bp66495326--.

Col. 5, Line 32, "Chr18g.66495327Ins227 bp66495326" should read as --Chr18g.66495327Ins227bp66495326--.

Col. 5, Line 35, "Chr18g.66495327Ins227 bp66495326" should read as --Chr18g.66495327Ins227bp66495326--.

Col. 5, Line 36, "Ins227 bp" should read as --Ins227bp--.

Col. 6, Line 24, "288 bp" should read as --288bp--.

Col. 6, Line 65-66, "Chr18g.66495327Ins227 bp66495326" should read as --Chr18g.66495327Ins227bp66495326--.

Col. 6, Line 66, "Ins227 bp" should read as --Ins227bp--.

Col. 7, Line 1, "Ins227 bp" should read as --Ins227bp--.

Col. 7, Line 36, "Chr18g.66495327Ins227 bp66495326" should read as --Chr18g.66495327Ins227bp66495326--.

Col. 7, Line 37, "Ins227 bp" should read as --Ins227bp--.

Col. 7, Line 39, "Ins227 bp" should read as --Ins227bp--.

Col. 7, Line 47-48, "Chr18g.66495327Ins227 bp66495326" should read as --Chr18g.66495327Ins227bp66495326--.

Col. 7, Line 50, "Ins227 bp" should read as --Ins227bp--.

Col. 7, Line 51, "Chr18g.66495327Ins227 bp66495326" should read as --Chr18g.66495327Ins227bp66495326--.

Col. 7, Line 55, "Chr18g.66495327Ins227 bp66495326" should read as --Chr18g.66495327Ins227bp66495326--.

CERTIFICATE OF CORRECTION (continued)
U.S. Pat. No. 9,249,470 B2

Col. 7, Line 58, "Chr18g.66495327Ins227 bp66495326" should read as --Chr18g.66495327Ins227bp66495326--.

Col. 7, Line 59, "Ins227 bp" should read as --Ins227bp--.

Col. 8, Line 33, "Ins227 bp" should read as --Ins227bp--.

Col. 10, Line 41, "227 bp" should read as --227bp--.

Col. 13, Line 50, "300 bp" should read as --300bp--.

Col. 13, Line 51, "(Ins227 bp)" should read as --(Ins227bp)--.

Col. 13, Line 64, "Chr18g.66495327Ins227 bp66495326" should read as --Chr18g.66495327Ins227bp66495326--.

Col. 13, Line 65, "(Ins227 bp)" should read as --(Ins227bp)--.

Col. 13, Line 67, "Ins227 bp" should read as --Ins227bp--.

Col. 14, Line 47, "-600 bp;" should read as -- -600bp;--.

Col. 14, Line 47, "Insertion227 bp" should read as --Insertion227bp--.

Col. 14, Line 47, "-827 bp" should read as -- -827bp--.

Col. 15, Line 4, "(Ins227 bp)" should read as --(Ins227bp)--.

Col. 15, Line 13, "Ins227 bp" should read as --Ins227bp--.

Col. 19, Line 34, "2155 bp" should read as --2155bp--.

Col. 19, Line 65, "2151 bp" should read as --2151bp--.

Col. 20, Line 23, "227 bp" should read as --227bp--.

Col. 20, Line 23-24, "Chr18:66495327-[Insertion227 bp]-66495326" should read as --Chr18:66495327-[Insertion227bp]-66495326--.

Col. 20, Line 24, "146 bp" should read as --146bp--.

Col. 21, Table 7, "Insertion 227 bp" should read as --Insertion227bp--.

Col. 21, Table 7, "Insertion 227 bp" should read as --Insertion227bp--.

Col. 21, Table 7, "[Insertion227 bp]" should read as --[Insertion227bp]--.

Col. 23, Line 15, "Ins227 bp" should read as --Ins227bp--.

Col. 23, Line 16, "(Chr18g.66495327Ins227 bp66495326)" should read as --(Chr18g.66495327Ins227bp66495326)--.

Col. 23, Line 19-20, "66495327Ins227 bp66495326" should read as --66495327Ins227bp66495326--.

Col. 23, Line 46, "Ins227 bp" should read as --Ins227bp--.

Col. 23, Line 48, "66495327Ins227 bp66495326" should read as --66495327Ins227bp66495326--.

Col. 24, Line 26, "Insertion227 bp" should read as --Insertion227bp--.

Col. 24, Line 26, "827 bp" should read as --827bp--.

Col. 24, Line 41, "Ins227 bp" should read as --Ins227bp--.

Col. 24, Line 43, "Ins227 bp" should read as --Ins227bp--.

Col. 24, Line 44, "Ins227 bp" should read as --Ins227bp--.

Col. 24, Line 48, "Ins227 bp" should read as --Ins227bp--.

Col. 24, Table 8, Sample ID 7, "Insertion227 bp/ Insertion227 bp" should read as --Insertion227bp/ Insertion227bp--.

Col. 24, Table 8, Sample ID 8, "Insertion227 bp/ Insertion227 bp" should read as --Insertion227bp/ Insertion227bp--.

Col. 24, Table 8, Sample ID 9, "Insertion227 bp/ Insertion227 bp" should read as --Insertion227bp/ Insertion227bp--.

Col. 24, Table 8, Sample ID 11, "Insertion227 bp/ Insertion227 bp" should read as --Insertion227bp/ Insertion227bp--.

Col. 24, Table 8, Sample ID 12, "Ins227 bp/Normal" should read as --Ins227bp/Normal--.

Col. 24, Table 8, Sample ID 3, "Ins227 bp/Normal" should read as --Ins227bp/Normal--.

Col. 25, Table 8, Sample ID 4, "Ins227 bp/Normal" should read as --Ins227bp/Normal--.

Col. 25, Table 8, Sample ID 10, "Ins227 bp/Normal" should read as --Ins227bp/Normal--.

CERTIFICATE OF CORRECTION (continued)

Col. 25, Table 8, Sample ID 13, "Ins227 bp/Normal" should read as --Ins227bp/Normal--.

Col. 25, Table 8, Sample ID 14, "Ins227 bp/Normal" should read as --Ins227bp/Normal--.

Col. 25, Line 16, "Ins227 bp" should read as --Ins227bp--.

Col. 25, Line 20, "Ins227 bp" should read as --Ins227bp--.

Col. 25, Line 25, "Ins227 bp" should read as --Ins227bp--.

Col. 25, Line 47, "227 bp" should read as --227bp--.

Col. 26, Line 16, "(Ins227 bp)" should read as --(Ins227bp)--.

Col. 26, Line 25, "Ins227 bp" should read as --Ins227bp--.

Col. 26, Line 30, "Ins227 bp" should read as --Ins227bp--.

Col. 28, Line 11, "Ins227 bp" should read as --Ins227bp--.

Col. 28, Line 22-23, "Ins227 bp" should read as --Ins227bp--.

Col. 28, Line 34, "Ins227 bp" should read as --Ins227bp--.

Col. 28, Line 40, "Ins227 bp" should read as --Ins227bp--.

Col. 28, Line 42, "Ins227 bp" should read as --Ins227bp--.

Col. 28, Line 46, "Ins227 bp" should read as --Ins227bp--.

Col. 28, Line 46, "1590 bp" should read as --1590bp--.

Col. 28, Line 49, "Ins227 bp" should read as --Ins227bp--.

Col. 28, Line 50, "Ins227 bp" should read as --Ins227bp--.

Col. 29, Line 25, "Chr18g.66495327Ins227 bp66495326" should read as
--Chr18g.66495327Ins227bp66495326--.

Col. 29, Line 48, "Ins227 bp" should read as --Ins227bp--.

Col. 29, Line 51, "(Ins227 bp/Ins227 bp" should read as --(Ins227bp/Ins227bp--.

Col. 29, Line 51, "Ins227 bp/Normal)" should read as --Ins227bp/Normal)--.

CERTIFICATE OF CORRECTION (continued)
U.S. Pat. No. 9,249,470 B2

Col. 29, Line 56, "Ins227 bp/Ins227 bp" should read as --Ins227bp/Ins227bp--.

Col. 29, Line 57, "Ins227 bp/Normal" should read as --Ins227bp/Normal--.

IN THE CLAIMS

Claim 1(c), Col. 55, Line 19, "Chr18g.66495327Ins227 bp66495326" should read as --Chr18g.66495327Ins227bp66495326--.

Claim 1(d)(i), Col. 55, Line 23, "Ins227 bp/Ins227 bp" should read as --Ins227bp/Ins227bp--.

Claim 1(d)(i), Col. 55, Line 24, "Chr18g.66495327Ins227 bp66495326" should read as --Chr18g.66495327Ins227bp66495326--.

Claim 1(d)(ii), Col. 55, Line 26, "Ins227 bp/normal" should read as --Ins227bp/normal--.

Claim 1(d)(ii), Col. 55, Line 27, "Chr18g.66495327Ins227 bp66495326" should read as --Chr18g.66495327Ins227bp66495326--.

Claim 1(d)(iii), Col. 55, Line 30, "Chr18g.66495327Ins227 bp66495326" should read as --Chr18g.66495327Ins227bp66495326--.

Claim 2, Col. 55, Lines 32-33, "Ins227 bp/Ins227 bp" should read as --Ins227bp/Ins227bp--.

Claim 2, Col. 55, Lines 33-34, "Chr18g.66495327Ins227 bp66495326" should read as --Chr18g.66495327Ins227bp66495326--.

Claim 3, Col. 55, Lines 37-38, "Ins227 bp/normal" should read as --Ins227bp/normal--.

Claim 3, Col. 55, Lines 38-39, "Chr18g.66495327Ins227 bp66495326" should read as --Chr18g.66495327Ins227bp66495326--.

Claim 4, Col. 55, Lines 41-42, "normal/ normal" should read as --normal/normal--.

Claim 4, Col. 55, Lines 42-43, "Chr18g.66495327Ins227 bp66495326" should read as --Chr18g.66495327Ins227bp66495326--.

Claim 9(a), Col. 55, Line 57, "Chr18g.66495327Ins227 bp66495326" should read as --Chr18g.66495327Ins227bp66495326--.

Claim 9(b), Col. 55, Line 60, "Chr18g.66495327Ins227 bp66495326" should read as --Chr18g.66495327Ins227bp66495326--.

Claim 9(c)(i), Col. 55, Line 67, "Ins227 bp/Ins227 bp" should read as --Ins227bp/Ins227bp--.

CERTIFICATE OF CORRECTION (continued)
U.S. Pat. No. 9,249,470 B2

Claim 9(c)(i), Col. 56, Line 12, "Chr18g.66495327Ins227 bp66495326" should read as --Chr18g.66495327Ins227bp66495326--.

Claim 9(c)(ii), Col. 56, Line 17, "Chr18g.66495327Ins227 bp66495326" should read as --Chr18g.66495327Ins227bp66495326--.

Claim 9(c)(iii), Col. 56, Line 22, "Chr18g.66495327Ins227 bp66495326" should read as --Chr18g.66495327Ins227bp66495326--.

Claim 9(c)(iii), Col. 56, Line 24, "Ins227 bp/Ins227 bp" should read as --Ins227bp/Ins227bp--.

Claim 9(c)(iii), Col. 56, Line 25, "Chr18g.66495327Ins227 bp66495326" should read as --Chr18g.66495327Ins227bp66495326--.

Claim 9(c)(iv), Col. 56, Line 29, "Ins227 bp/Ins227 bp" should read as --Ins227bp/Ins227bp--.

Claim 9(c)(iv), Col. 56, Line 30, "Chr18g.66495327Ins227 bp66495326" should read as --Chr18g.66495327Ins227bp66495326--.

Claim 9(c)(iv), Col. 56, Line 32, "Ins227 bp/normal" should read as --Ins227bp/normal--.

Claim 9(c)(iv), Col. 56, Line 33, "Chr18g.66495327Ins227 bp66495326" should read as --Chr18g.66495327Ins227bp66495326--.

Claim 9(c)(v), Col. 56, Line 39, "Chr18g.66495327Ins227 bp66495326" should read as --Chr18g.66495327Ins227bp66495326--.

Claim 9(c)(v), Col. 56, Line 41, "Ins227 bp/normal" should read as --Ins227bp/normal--.

Claim 9(c)(v), Col. 56, Line 42, "Chr18g.66495327Ins227 bp66495326" should read as --Chr18g.66495327Ins227bp66495326--.

Claim 9(c)(vi), Col. 56, Line 47, "Ins227 bp/normal" should read as --Ins227bp/normal--.

Claim 9(c)(vi), Col. 56, Line 48, "Chr18g.66495327Ins227 bp66495326" should read as --Chr18g.66495327Ins227bp66495326--.

Claim 10, Col. 56, Line 53, "Ins227 bp/Ins227 bp" should read as --Ins227bp/Ins227bp--.

Claim 10, Col. 56, Line 54, "Chr18g.66495327Ins227 bp66495326" should read as --Chr18g.66495327Ins227bp66495326--.

Claim 11, Col. 56, Line 59, "Chr18g.66495327Ins227 bp66495326" should read as --Chr18g.66495327Ins227bp66495326--.

CERTIFICATE OF CORRECTION (continued)
U.S. Pat. No. 9,249,470 B2

Claim 12, Col. 56, Line 63, "Chr18g.66495327Ins227 bp66495326" should read as --Chr18g.66495327Ins227bp66495326--.

Claim 12, Col. 56, Line 64-65, "Ins227 bp/Ins227 bp" should read as --Ins227bp/Ins227bp--.

Claim 12, Col. 56, Lines 65-66, "Chr18g.66495327Ins227 bp66495326" should read as --Chr18g.66495327Ins227bp66495326--.

Claim 13, Col. 57, Line 2, "Ins227 bp/Ins227 bp" should read as --Ins227bp/Ins227bp--.

Claim 13, Col. 57, Line 3, "Chr18g.66495327Ins227 bp66495326" should read as --Chr18g.66495327Ins227bp66495326--.

Claim 13, Col. 57, Lines 4-5, "Ins227 bp/normal" should read as --Ins227bp/normal--.

Claim 13, Col. 57, Line 5-6, "Chr18g.66495327Ins227 bp66495326" should read as --Chr18g.66495327Ins227bp66495326--.

Claim 14, Col. 57, Line 11, "Chr18g.66495327Ins227 bp66495326" should read as --Chr18g.66495327Ins227bp66495326--.

Claim 14, Col. 57, Lines 12-13, "Ins227 bp/normal" should read as --Ins227bp/normal--.

Claim 14, Col. 57, Lines 13-14, "Chr18g.66495327Ins227 bp66495326" should read as --Chr18g.66495327Ins227bp66495326--.

Claim 15, Col. 57, Line 18, "Ins227 bp/normal" should read as --Ins227bp/normal--.

Claim 15, Col. 58, Line 1, "Chr18g.66495327Ins227 bp66495326" should read as --Chr18g.66495327Ins227bp66495326--.

Claim 16, Col. 58, Lines 6-7, "Chr18g.66495327Ins227 bp66495326" should read as --Chr18g.66495327Ins227bp66495326--.